US012653974B2

(12) United States Patent

Holley et al.

(10) Patent No.: US 12,653,974 B2
(45) Date of Patent: Jun. 16, 2026

(54) ACOUSTIC DETECTION FOR RESPIRATORY TREATMENT APPARATUS

(71) Applicant: ResMed Pty Ltd, Bella Vista (AU)

(72) Inventors: Liam Holley, Sydney (AU); Dion Charles Chewe Martin, Sydney (AU); Steven Paul Farrugia, Sydney (AU)

(73) Assignee: ResMed Pty Ltd (AU)

( * ) Notice: Subject to any disclaimer, the term of this patent is extended or adjusted under 35 U.S.C. 154(b) by 49 days.

(21) Appl. No.: 18/927,378

(22) Filed: Oct. 25, 2024

(65) Prior Publication Data

US 2025/0177670 A1 Jun. 5, 2025

Related U.S. Application Data

(60) Continuation of application No. 16/947,676, filed on Aug. 12, 2020, now Pat. No. 12,144,924, which is a (Continued)

(30) Foreign Application Priority Data

Feb. 11, 2009 (AU) ................................. 2009900561

(51) Int. Cl.
*A61M 16/00* (2006.01)
*A61B 5/087* (2006.01)
(Continued)

(52) U.S. Cl.
CPC ......... *A61M 16/0069* (2014.02); *A61B 5/087* (2013.01); *A61B 5/097* (2013.01);
(Continued)

(58) Field of Classification Search
CPC .................................................. A61M 16/0069
See application file for complete search history.

(56) References Cited

U.S. PATENT DOCUMENTS 4,326,416 A 4/1982 Fredberg
5,251,261 A 10/1993 Meyer et al.
(Continued)

FOREIGN PATENT DOCUMENTS

CN 1468077 A 1/2004
EP 0661071 A1 7/1995
(Continued)

OTHER PUBLICATIONS

EP Search Report dated Mar. 11, 2020—EP Application No. 19187766. 1.

(Continued)

*Primary Examiner* — Hee K Song

(74) *Attorney, Agent, or Firm* — Botos Churchill IP Law LLP

(57) ABSTRACT

Methods and apparatus provide acoustic detection for automated devices such as respiratory treatment apparatus. In some embodiments of the technology, acoustic analysis of noise or sound pulses, such as a cepstrum analysis, based on signals of a sound sensor permits detection of obstruction such as within a patient interface, mask or respiratory conduit or within patient respiratory system. Some embodiments further permit detection of accessories such as an identification thereof or a condition of use thereof, such as a leak. Still further embodiments of the technology permit the detection of a patient or user who is intended to use the automated device.

30 Claims, 26 Drawing Sheets

Related U.S. Application Data division of application No. 13/148,730, filed as application No. PCT/AU2010/000140 on Feb. 10, 2010, now Pat. No. 10,773,038.

(60) Provisional application No. 61/253,172, filed on Oct. 20, 2009, provisional application No. 61/233,554, filed on Aug. 13, 2009.

(51) Int. Cl.

| | |
|---|---|
| *A61B 5/097* | (2006.01) |
| *A61B 7/00* | (2006.01) |
| *A61M 16/16* | (2006.01) |
| *A61B 5/00* | (2006.01) |

(52) U.S. Cl.
CPC ......... *A61B 7/003* (2013.01); *A61M 16/0051* (2013.01); *A61M 16/026* (2017.08); *A61M 16/16* (2013.01); *A61B 5/7257* (2013.01); *A61M 2016/0027* (2013.01); *A61M 2016/0036* (2013.01); *A61M 2205/15* (2013.01); *A61M 2205/3365* (2013.01); *A61M 2205/3375* (2013.01); *A61M 2205/505* (2013.01); *A61M 2205/52* (2013.01); *A61M 2230/46* (2013.01)

(56) References Cited

U.S. PATENT DOCUMENTS

| | | | |
|---|---|---|---|
| 5,445,144 A | | 8/1995 | Wodicka et al. |
| 5,677,984 A | * | 10/1997 | Mitome ................. G10L 25/48 |
| | | | 704/231 |
| 5,681,339 A | | 10/1997 | McEwen et al. |
| 5,704,345 A | | 1/1998 | Berthon-Jones |
| 6,363,933 B1 | | 4/2002 | Berthon-Jones |
| 6,436,057 B1 | | 8/2002 | Goldsmith et al. |
| 6,666,830 B1 | | 12/2003 | Lehrman et al. |
| 6,895,963 B1 | | 5/2005 | Martin et al. |
| 6,948,497 B2 | | 9/2005 | Zdrojkowski et al. |
| 7,469,698 B1 | | 12/2008 | Childers et al. |
| 2002/0057805 A1 | * | 5/2002 | Kato ..................... G06V 40/10 |
| | | | 381/59 |
| 2003/0034035 A1 | | 2/2003 | Raphael |
| 2004/0118403 A1 | | 6/2004 | O'Connor et al. |
| 2004/0225226 A1 | | 11/2004 | Lehrman et al. |
| 2005/0005935 A1 | | 1/2005 | Gradon |
| 2006/0027234 A1 | | 2/2006 | Gradon |
| 2006/0037615 A1 | | 2/2006 | Wilkinson et al. |
| 2009/0151725 A1 | | 6/2009 | Childers |
| 2009/0301488 A1 | * | 12/2009 | Sun ................... A61M 16/0051 |
| | | | 128/204.23 |
| 2010/0006097 A1 | | 1/2010 | Frater et al. |
| 2010/0163047 A1 | * | 7/2010 | Probst ..................... A62B 9/00 |
| | | | 128/205.29 |
| 2011/0162647 A1 | | 7/2011 | Hubby et al. |
| 2018/0064402 A1 | | 3/2018 | Leydon |

FOREIGN PATENT DOCUMENTS

| | | | | |
|---|---|---|---|---|
| EP | 1800705 A2 | 6/2007 | | |
| JP | 2000292416 A | 10/2000 | | |
| JP | 2001500028 A | 1/2001 | | |
| JP | 2004533270 A | 11/2004 | | |
| JP | 5738201 B2 | 6/2015 | | |
| WO | 9311703 A1 | 6/1993 | | |
| WO | 2001091843 A1 | 12/2001 | | |
| WO | WO-0191843 A1 | * 12/2001 | ........... | A61M 25/01 |
| WO | 0228281 A1 | 4/2002 | | |
| WO | 2003000015 A2 | 1/2003 | | |
| WO | 03015610 A2 | 2/2003 | | |
| WO | 2003015610 A2 | 2/2003 | | |
| WO | 2003024335 A1 | 3/2003 | | |
| WO | 2006092001 A1 | 9/2006 | | |
| WO | 2008025080 A1 | 3/2008 | | |
| WO | 2010091462 A1 | 8/2010 | | |

OTHER PUBLICATIONS

EP Search Report for Application No. 10740837 dated Apr. 23, 2015.

EPO Examination Report in EP Application No. 19187766.1 dated Jan. 3, 2022.

Extended European Search Report from corresponding EP Application No. 23168389.7 dated Oct. 16, 2023 (9 pp.).

First Office Action in CN Application No. 20191127068, dated Dec. 10, 2021, with English translation.

International Search Report and Written Opinion dated May 10, 2010 for PCT/AU2010/000140.

Office Action for corresponding CN Application No. 201911270687X dated Jul. 20, 2022 with English Translation.

Childers, Donald G, et al., "The Cepstrum: A Guide to Processing"; Proceedings of the IEEE, vol. 65, No. 10, Oct. 1977.

Familari, Peter, et al., "Acoustic ear-scanning the new solution to identify theft", news.com.au, Herald Jul. 29, 2009, http://www.news. com.au/technology/story/0, 28348,25851576-5014239,000.html.

Jarreau, et al., "Detection of Positional Airway Obstruction in Neonates by Acoustic Reflection", American Journal of Respiratory and Critical Medicine, vol. 161 2000, pp. 1754-1756.

Klarskov, N, et al., 'Pressure Reflectometry: in vitro recordings with a new technique for simultaneous measurement of cross-sectional area and pressure in a collapsible tube', Physiological Measurement, 2005, vol. 26, pp. 269-280.

Mansfield, J.P., et al., 'Using Acoustic Reflectometry to Determine Breathing Tube Position and Patency', Journal of Sound and Vibration, 1995, vol. 188, Issue 2, pp. 167-188.

Randall, RB, "Frequency Analysis", Copenhagen: Bruel & Kjaer, p. 344 (1977, revised ed. 1987).

Taghvaei, M., et al., 'Leak detection in pipelines using cepstrum analysis', Measurement Science and Technology, 2006, vol. 17, pp. 367-372.

* cited by examiner

220    Determine with a sound sensor a measure of sound of a flow generator within a respiratory treatment conduit.

222    Analyze the measure of sound from the sound sensor.

224    Indicate a presence or absence of obstruction in the respiratory tube based on the analyzing Quefrency (s)

Quefrency (s)

800

872

882

884

1104

1102

Sound
Sensor

1108

1104

Respiratory Tube
Obstruction
Detection
Controller

Obstructed = Yes
Position = 3 inches from
patient end
Extent = 45%

1110

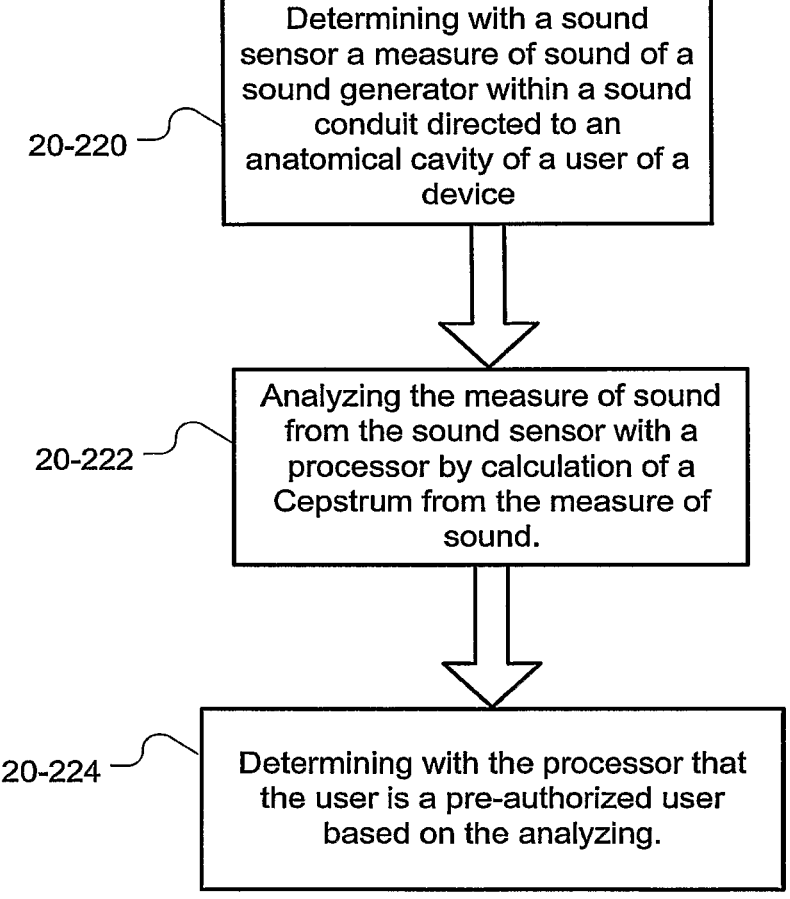

20-220

Determining with a sound sensor a measure of sound of a sound generator within a sound conduit directed to an anatomical cavity of a user of a device 20-222

Analyzing the measure of sound from the sound sensor with a processor by calculation of a Cepstrum from the measure of sound.

20-224

Determining with the processor that the user is a pre-authorized user based on the analyzing.

Fig. 20

Quefrency (s)

Quefrency (s)

ACOUSTIC DETECTION FOR RESPIRATORY TREATMENT APPARATUS

CROSS-REFERENCE TO RELATED APPLICATIONS

This application is a continuation of U.S. application Ser. No. 16/947,676, filed on Aug. 12, 2020, which is a divisional of U.S. patent application Ser. No. 13/148,730 filed on Aug. 10, 2011, now U.S. Pat. No. 10,773,038, which is a national phase entry under 35 U.S.C. § 371 of International Application No. PCT/AU2010/000140 filed Feb. 10, 2010, published in English, which claims priority from U.S. Provisional Patent Application No. 61/253,172 filed Oct. 20, 2009, U.S. Provisional Patent Application No. 61/233,554 filed Aug. 13, 2009, which claims priority from Australian Provisional Patent Application No. 2009900561, filed Feb. 11, 2009, all of which are incorporated herein by reference.

FIELD OF THE TECHNOLOGY

The present technology relates to methods and apparatus for acoustic detection that may be useful for automated devices such as respiratory treatment apparatus. Embodiments of the technology may involve detection of obstruction such as within a patient interface or patient respiratory system, detection of accessories or condition thereof, such as a mask, and detection of a patient or use

BACKGROUND OF THE TECHNOLOGY

Respiratory treatment apparatus, such as a ventilator or positive pressure treatment device, may typically include a flow generator, an air filter, a mask, cannula or endotracheal tube, a supply tube connecting the flow generator to the mask or tube, sensors and a microprocessor-based controller. The flow generator may be a servo-controlled motor and an impeller (e.g., a blower). Optionally, the flow generator may also include a valve capable of discharging air to atmosphere as a means for altering the pressure delivered to the patient as an alternative to motor speed control of a blower. The sensors measure, amongst other things, motor speed, gas volumetric flow rate and outlet pressure, such as with a pressure transducer, flow sensor or the like.

Such devices have been automated for making changes to the system. For example, CPAP devices have been implemented to detect a condition of the patient. In U.S. Pat. No. 5,704,345 to Berthon-Jones, a device is described which automatically adjusts treatment pressure in response to indications of partial or complete upper airway obstruction. An automated procedure disclosed by Berthon-Jones involves detecting an open or closed patient airway by inducing airflow with a CPAP pressure generator that produces a modulated pressure output. The air flow induced by the pressure modulation is separated from air flow induced by other factors (such as heartbeat), by demodulating the measured air flow signal. Apneas are classified as "airway open" if the mean induced signal is more then 0.03 l/sec, and "airway closed" if the mean induced signal is less than 0.03 l/sec.

In the Patent Cooperation Treaty Published Patent Application No. WO2006/092001, Kwok describes a system of identifying masks by the use of a coded series of resistors. The controller may detect the mask by identifying a particular electrical resistance based on the resistors that is associated with the identity of particular masks.

It may be desirable for improved techniques and devices for assessing the state of such systems or controlling the operations thereof.

BRIEF SUMMARY OF THE TECHNOLOGY

An aspect of the present technology is to implement acoustic detection for various purposes.

Another aspect of the present technology is to implement acoustic detection in or with devices capable of emitting sound or noise.

Another aspect of the present technology is to implement acoustic detection in or with respiratory treatment apparatus.

Another aspect of the present technology is to implement acoustic detection by, for example, cepstrum analysis.

Still further aspects of the present technology are to implement obstruction detection, component or accessory detection and/or patient or user detection by acoustic analysis.

A. Obstruction Detection

One aspect of certain example embodiments of the present technology is to automate a detection of obstruction.

Another aspect of certain example embodiments of the present technology is to automate a detection of obstruction within a respiratory apparatus conduit.

Another aspect of some embodiments of the present technology include methods that detect a respiratory treatment conduit obstruction by determining with a sound sensor a measure of sound of a flow generator within a respiratory treatment conduit, such as an endotracheal tube. The measure of sound may then be analyzed with a processor. The processor may then indicate a presence or absence of obstruction in the respiratory treatment conduit based on the analyzing.

In some embodiments, the analysis may involve calculating a Fourier transform from data samples representing the measure of sound. This may further involve calculating a logarithm of the transformed data samples representing the measure of sound. Still further, the analyzing may include calculating an inverse transform of the logarithm of the transformed data samples representing the measure of sound. In some embodiments, the analyzing may also involve calculating a difference between (a) the inverse transform of the logarithm of the transformed data samples representing the measure of sound and (b) an inverse transform of a logarithm of Fourier transformed data samples representing a sound measured from an unobstructed version of the respiratory treatment conduit.

In still further embodiments, the indicating may involve displaying a graph of data on a display based on the difference calculating. Moreover, a location and extent of the presence of obstruction based on data of the difference calculating may be determined. Such an extent may optionally be determined from an amplitude or magnitude value of a significant sample of the data of the difference calculating. The location may be determined from a time of the significant sample in the data of the difference calculating. Optionally, the sound source that generates the sound within the respiratory treatment conduit may be a flow generator. Still further, the sound sensor may be a single microphone.

Some embodiments of the technology also involve an apparatus for detecting a respiratory treatment conduit obstruction. The apparatus may include a microphone adapted for coupling with a respiratory treatment conduit to generate a measure of sound of a flow generator within the respiratory treatment conduit. A processor of the apparatus may be configured to analyze data samples of the measure of sound from the microphone and to indicate a presence or absence of obstruction in the respiratory treatment conduit based on the analyzed data samples. Optionally, the microphone may be adapted with an endotracheal tube coupler having an opening to connect with a portion of an endotracheal tube. The endotracheal tube coupler may also include an opening adapted to connect with a portion of a ventilator supply tube. The coupler may further include a microphone chamber adapted with a membrane to separate the chamber from a gas channel of the coupler. Optionally, the coupler may further include a vent adapted to permit the microphone chamber to equalize with ambient pressure. In some embodiments, the apparatus may also include a flow generator and the processor may be configured to control the flow generator to generate a respiratory treatment. Similarly, the processor may be configured to determine obstruction in accordance with any of the previously described methods.

In some embodiments of the technology, a method implements detecting of respiratory system obstruction. The method may include determining with a sound sensor a measure of sound of a flow generator. A processor may then analyze the measure of sound from the sound sensor by calculation of a cepstrum from the measure of sound. The processor may then indicate a presence or absence of obstruction (e.g., partial or full) in the respiratory system of a patient based on the analyzing. In some embodiments, this may involve detecting an extent of the presence of obstruction based on calculating a difference between the cepstrum from the measure of sound and a cepstrum determined from a prior measure of sound. Optionally, the extent may be determined from an amplitude value of a significant sample of the data of the difference calculating. Moreover, a location may be determined from a position of the significant sample in the data of the difference calculating, such that the position represents a point beyond a known end of a respiratory treatment conduit.

Such methods may be implemented in an apparatus for detecting a respiratory obstruction. For example, the apparatus may include a microphone adapted for coupling with a respiratory treatment conduit to generate a measure of sound of a flow generator. The apparatus may also include a controller or processor configured to analyze data samples of the measure of sound from the microphone by calculation of a cepstrum with the data samples of the measure of sound. The apparatus may be further configured to indicate a presence or absence of obstruction in the respiratory system of a patient based on the analyzed data samples. The apparatus may also optionally include a flow generator, where the controller or processor is further adapted to control the flow generator to generate a respiratory treatment.

B. Accessory Detection

One aspect of the technology is directed towards a recognition system that provides structure to facilitate the coordination between the flow generator and the peripheral components.

Another aspect of the present technology is to provide methods and apparatus for automatic detection of the type of mask connected to a CPAP device. Further aspects of the present technology may include: methods, systems and devices to detect and/or identify characteristics in the airpath of CPAP device including patient interfaces, and patient's respiratory systems.

Another aspect of the technology relates to an adapter for use with a flow generator that generates a supply of pressurized air to be provided at an outlet to a patient for treatment. The adapter includes a conduit attachable to the outlet of the flow generator, and an identifying element supported by the conduit and providing an identifying feature unique to a specific peripheral component attachable to the flow generator. The identifying feature is communicatable to the flow generator so that appropriate operating parameters of the flow generator may be automatically selected by the flow generator to coordinate with the specific peripheral component.

C. Patient/User Detection

An aspect of certain example embodiments of the present technology is to automate a method of detection or authentication of a user of a device.

Another aspect of certain example embodiments of the present technology is to automate a detection of particular user of a device so as to preclude or permit operations(s) in accordance with the detected user.

Another aspect of certain example embodiments of the present technology is to automate a detection of particular user of a respiratory treatment apparatus as a safety feature.

A still further aspect of example embodiments of the technology is a method for authenticating a user of a device including determining with a sound sensor a measure of sound of a sound generator within a sound conduit directed to an anatomical cavity of a user of a device. The method may further involve analyzing the measure of sound from the sound sensor with a processor by calculation of a cepstrum from the measure of sound. The method may still further involve determining with the processor that the user is a pre-authorized user based on the analyzing.

In some embodiments, the determining in the method may include permitting an operation of the device. In some embodiments, the sound generator comprises a speaker and the sound sensor comprises a microphone. In some embodiments, the device protected by the authentication is a respiratory treatment apparatus where the sound generator includes a flow generator and the sound conduit includes a respiratory supply tube. In some cases, the analyzing may involve comparing data of the cepstrum with data of a prior cepstrum determined from a prior measure of sound in a setup process. In some such cases, the method may include determining a prior measure of sound taken in a setup process.

In some embodiments, the technology may include an apparatus for authenticating a user. The apparatus may include a sound conduit adapted to direct an acoustic signal to an anatomical cavity of a user of the apparatus. The apparatus may also include a sound generator to generate the acoustic signal. The apparatus may further include a microphone adapted for coupling with the sound conduit to generate a measure of the acoustic signal. The apparatus may also include a processor configured to analyze data samples of the measure of the acoustic signal from the microphone by calculation of a cepstrum with the data samples of the measure of sound. The processor may also be configured to determine that the user is a pre-authorized user based on the analysis.

In some of the embodiments, the processor may be configured to permit an operation of the apparatus based on the determination. The sound generator of the apparatus may include at least one speaker. The processor of the apparatus may also optionally conduct the analysis by comparing data of the cepstrum with data of a prior cepstrum determined from a prior measure of sound taken in a setup process. In some embodiments, the processor of the apparatus may also be configured to set the prior measure in a setup process. In some embodiments, the apparatus may be a respiratory treatment apparatus where the sound generator is a servo-controlled blower and the sound conduit comprises a respiratory supply tube and mask or nasal cannula.

Other features of the technology will be apparent from consideration of the information contained in the following detailed description, drawings and claims.

BRIEF DESCRIPTION OF THE DRAWINGS

The present technology is illustrated by way of example, and not by way of limitation, in the figures of the accompanying drawings, in which like reference numerals refer to similar elements including:

FIG. 20 is an example methodology for user detection of a device of the present technology;

DETAILED DESCRIPTION

Figure 1:
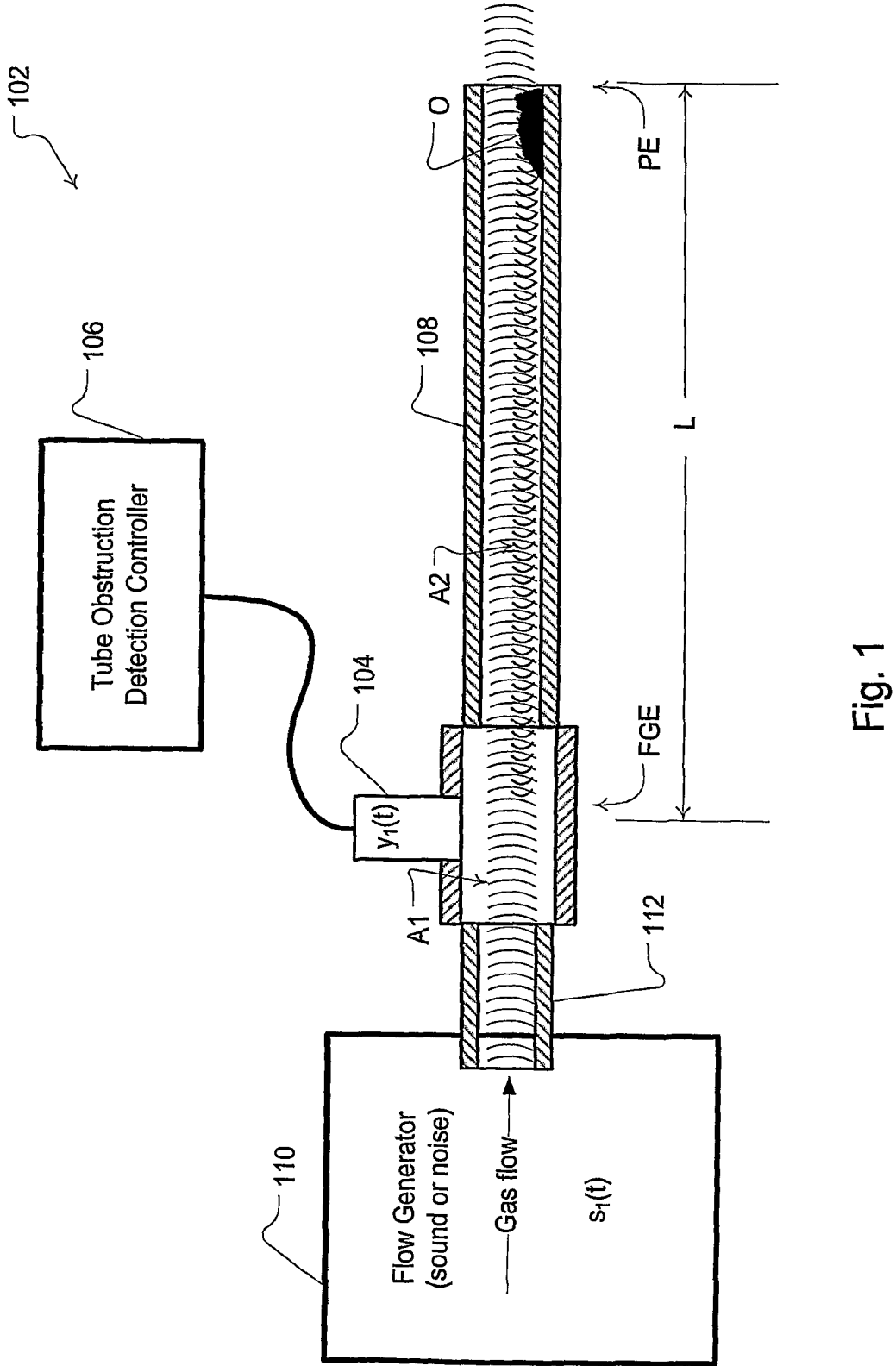
FIG. 1 illustrates example components of a system for detecting respiratory treatment conduit obstruction of the present technology.

Some embodiments of the present acoustic detection technologies may implement cepstrum analysis. A cepstrum may be considered the inverse Fourier Transform of the log spectrum or the forward Fourier Transform of the decibel spectrum, etc. The operation essentially can convert a convolution of an impulse response function IRF and a noise or sound source into an addition operation so that the noise or sound source may then be more easily accounted for or removed so as to isolate data of the system impulse response function for analysis. Techniques of cepstrum analysis are described in detail in a scientific paper entitled "The Cepstrum: A Guide to Processing" (Childers et al, Proceedings of the IEEE, Vol. 65, No. 10, October 1977) and RANDALL R B, Frequency Analysis, Copenhagen: Bruel & Kjaer, p. 344 (1977, revised ed. 1987). Other references describing cepstrum analysis may be available.

Such a method may be understood in terms of the property of convolution. The convolution of $f$ and g can be written as $f*g$. This operation may be the integral of the product of the two functions ($f$ and g) after one is reversed and shifted. As such, it is a type of integral transform as follows:

$$(f*g)(t) \stackrel{def}{=} \int_{-\infty}^{\infty} f(\tau) \cdot g(t-\tau) \, d\tau$$

While the symbol t is used above, it need not represent the time domain. But in that context, the convolution formula can be described as a weighted average of the function $f(\tau)$ at the moment t where the weighting is given by $g(-\tau)$ simply shifted by amount t. As t changes, the weighting function emphasizes different parts of the input function.

More generally, if $f$ and g are complex-valued functions on $R^d$, then their convolution may be defined as the integral $$(f*g)(x) = \int_{R^d} f(y)g(x-y) \, dy = \int_{R^d} f(x-y)g(y) \, dy.$$

A mathematical model that can relate an acoustic system output to the input for a time-invariant linear system, such as one involving conduits of a respiratory treatment apparatus, (which may include some human or other unknown part of the system) can be based on this convolution. The output measured at a microphone of the system may be considered as the input noise "convolved" with the system Impulse Response Function (IRF) as a function of time (t).

$$y(t) = s_1(t) * h_1(t) \qquad \text{Equation 1}$$

Where:
* denotes the convolution function.
y(t) is the signal measured at the microphone.
$s_1$(t) is the sound or noise source such as a noise or sound created in or by a flow generator ("FG") of a respiratory treatment apparatus.
$h_1$(t) is the system IRF from the noise or sound source to the microphone.

The Impulse Response Function (IRF) is the system response to a unit impulse input.

Conversion of equation 1 into the frequency domain by means of the Fourier Transform of the measured sound data (e.g., a discrete Fourier Transform ("DFT") or a fast Fourier transform ("FFT")) and considering the Convolution Theorem, the following equation, where the arrow represents performing the Fourier Transform, is produced:

$$y(t) = s_1(t) * h_1(t) \to Y(f) = S_1(f) \cdot H_1(f) \qquad \text{Equation 2}$$

Where:
Y(f) is the Fourier Transform of y(t);
$S_1$(f) is the Fourier Transform of $s_1$(t); and
$H_1$(f) is the Fourier Transform of $h_1$(t).
In such a case, convolution in the time domain becomes a multiplication in the frequency domain.

A logarithm of equation 2 may be applied so that the multiplication is converted into an addition:

$$\text{Log}\{Y(f)\} = \text{Log}\{S_1(f) \cdot H_1(f)\} = \text{Log}\{S_1(f)\} + \text{Log}\{H_1(f)\} \qquad \text{Equation 3}$$

Equation 3 may then be converted back into the time domain, by an Inverse Fourier Transform (IFT) (e.g., an inverse DFT or inverse FFT), which results in a Complex Cepstrum ($K(\tau)$) (Complex because we may work from the complex spectrum)—the inverse Fourier Transform of the logarithm of the spectrum.

$$K(\tau) = IFT[\text{Log}\{S_1(f)\} + \text{Log}\{H_1(f)\}] \qquad \text{Equation 4}$$

"$\tau$" is a real valued variable known as quefrency, with units measured in seconds. So we can see that effects that are convolutive in the time domain become additive in the logarithm of the spectrum, and remain so in the cepstrum.

Consideration of the data from a cepstrum analysis, such as examining the data values of the quefrency, may provide information about the system. For example, by comparing cepstrum data of a system from a prior or known baseline of cepstrum data for the system, the comparison, such as a difference, can be used to recognize differences or similarities in the system that may then be used to implement automated control for varying functions or purposes.

The following example embodiments may utilize the methodologies of such an analysis as herein explained to implement different detectors useful for various purposes.

A. Obstruction Detection

Invasively ventilated patients may be treated with ventilator devices by tracheal intubation. A flexible endotracheal tube is inserted into the trachea of the patient. The tube may then be connected to the respiratory treatment apparatus, which may optionally be a mechanical ventilator. The tube directs a flow of ventilatory support from the ventilator to the lungs to enable patient ventilation. The tube ensures that the patient's airways remain open or unobstructed for the delivery of the support. However, in some cases, biomaterial such as mucus may build up on the inside of the tube. The presence of a significant amount of such material can cause extra pneumatic resistance in the tube.

If the resistance caused by this material becomes too great, it can interfere with ventilation support. In such cases, the patient must be extubated so that the tube may either be replaced or cleaned. In some cases, an endotracheal camera may be utilized to inspect the interior of the tube and monitor the progression of any buildup in the tube. However, this is not an easy procedure and such a camera can be costly.

Thus, embodiments of the present technology may involve methods and devices for the detection of obstruction within respiratory treatment apparatus conduits such as an endotracheal tube or supply tube and mask. As illustrated in FIG. 1, the respiratory treatment conduit obstruction detection apparatus 102 may be implemented to detect the presence of obstruction (e.g., partial or otherwise), such as mucus or other bio-substance, within a conduit by sound wave measurement and analysis. Such a detector apparatus will typically include a sound sensor 104, such as a microphone, and a detection controller 106.

In a typical embodiment, the sound sensor 104 measures sound traversing within a respiratory treatment conduit 108 for analysis by the detection controller 106. For example, the sound may be that generated by a sound source. The sound may be the vibrations or sound created by the operation of a flow generator 110 such as a servo-controlled blower. For example, the flow generator may be supplying a flow of breathable gas via an optional supply conduit 112 to the respiratory treatment conduit 108. In the case where the respiratory treatment conduit 108 is within the respiratory system of the patient, the breathable gas may thereby provide a respiratory treatment to the patient. This measured sound may include sound waves reflected from an obstruction (illustrated by reference character "O" in FIG. 1) in the respiratory treatment conduit when present.

A sound signal from the sound sensor 104 can be sent to the detection controller 106. Optional analog-to-digital (A/D) converters/samplers (not shown separately) may be utilized in the event that supplied signal from the sensor is not in digital form and the controller is a digital controller. Based on the signal from the sensor, the controller assesses the sound signal to determine obstruction data, such as the presence or absence of obstruction, an extent of obstruction or a position of the obstruction in the respiratory treatment conduit.

In some embodiments, the detection controller 106 may include a processor configured to implement particular detection methodologies such as the algorithms described in more detail herein. Thus, the controller may include integrated chips, a memory and/or other control instruction, data or information storage medium. For example, programmed instructions encompassing such a detection methodology may be coded on integrated chips in the memory of the device. Such instructions may also or alternatively be loaded as software or firmware using an appropriate data storage medium. With such a controller or processor, the device can be used for determining and analyzing sound data from the sound sensor. Thus, the processor may control the assessment of obstruction as described in the embodiments discussed in more detail herein.

Figure 2:
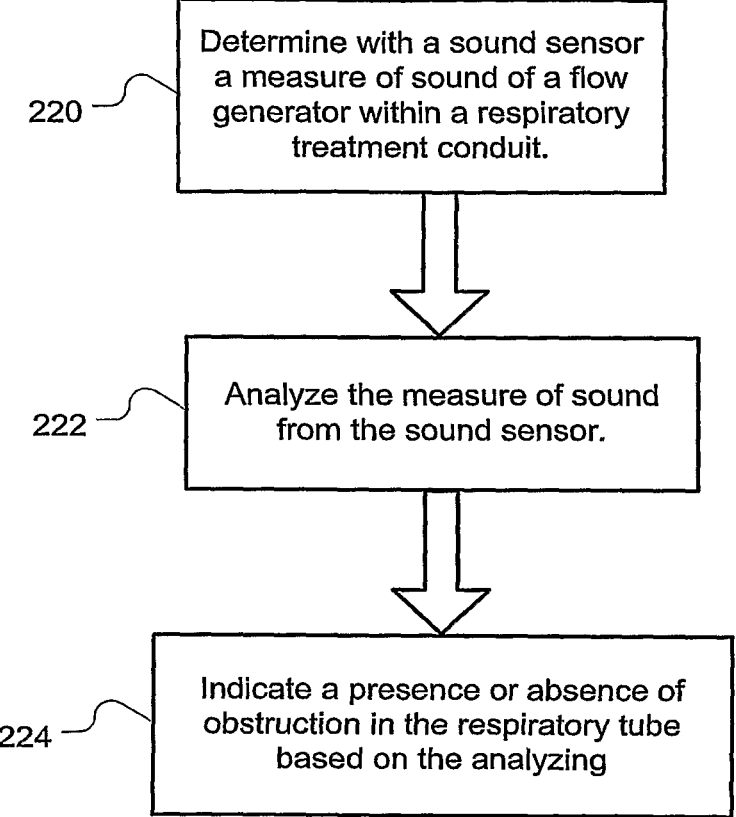
FIG. 2 is an example methodology for a device that may implement respiratory treatment conduit obstruction detection of the present technology.

One example of such a methodology or algorithm of the controller 106 of the respiratory treatment conduit obstruction detection apparatus 102 is illustrated in the flow chart of FIG. 2. At 220, a sound sensor measures sound of a flow generator within a respiratory treatment conduit, such as under the control of the controller. At 222, the measure of sound from the sound sensor is analyzed by the controller or a processor thereof. At 222, the controller or processor indicates a presence or absence of obstruction in the respiratory treatment conduit based on the analyzing.

In such an embodiment of the technology, there may be a number of design considerations relating to the acoustic nature of the system. The patient ventilator circuit can have many different variations in terms of the combination and permutation of components. Each combination may have different acoustic properties. One common component to these combinations may be a respiratory treatment conduit 108, such as an endotracheal tube, with an approximately constant cross section along its length "L" (when it is not obstructed), with the patient at a patient end of the conduit (shown as "PE" in FIG. 1), and the ventilator circuit (with other potential components) at the flow generator end (shown as "FGE" in FIG. 1). An acoustic characteristic of the conduit (when not obstructed) may be that it acts as a wave guide for a wide range of frequencies along its length. Thus, there may be no significant change in an acoustic signal as it propagates down the endotracheal tube other than the time delay associated with its propagation speed.

Another factor to consider may be that the flow generator or ventilator and patient can both be sources of random, cyclostationary, and deterministic noise. In addition, flow induced noise can be the result of the structural design of the components where there is flow in the system (e.g., supply conduits, etc.).

Thus, in some embodiments of the apparatus, detecting a change may be based on the acoustic reflection in a conduit (or endotracheal tube) during flow generator operations as the conduit becomes increasingly obstructed by a build up of material on its internal walls by comparison to when it was unobstructed. When the tube is clean or new, it can be free from obstruction. The Impulse Response Function ("IRF") of the sound or noise in such a system created by a flow generator of a ventilator circuit serving as a sound source to a sound sensor, can contain (or be considered) a delta function at a chosen time zero, and a reflection from the patient end PE of the tube at time 2L/c, where the speed of sound is denoted by "c", and the length of the conduit or endotracheal tube is "L". Thereafter, if the tube becomes partially obstructed by an obstruction O along its length, another IRF of the system may now contain a new reflection from the obstruction, at time 2x/c, where "x" is the distance from the sound sensor to the obstruction.

One potential method for monitoring for such a change in the reflection from the conduit or endotracheal tube may be based on the calculation of a cepstrum of a signal from the sound sensor. By comparing cepstrum data from a known clean conduit with cepstrum data from a potentially obstructed conduit, the comparison, such as differences there between, may be considered in identifying obstruction in the conduit. For example, if a common noise source is used from both tests, such as the same type of ventilator circuit or flow generator operating at the same settings (e.g., pressure delivery, speed and/or flow etc.), the comparison or difference between the cepstrum of the unobstructed tube and the cepstrum of the obstructed tube may be implemented to indicate, for example, (a) the existence of obstruction of the conduit, (b) location of the obstruction in the conduit, and/or (c) an extent of the obstruction, such as by consideration of an amplitude or magnitude of the difference data.

The Impulse Response Function (IRF) is the system response to a unit impulse input. Some factors of the IRF (from the flow generator as a sound source to the microphone response) are herein explained. When the conduit acts as a wave guide for sound produced by the flow generator. Sound is emitted and forms a first signal (illustrated in FIG. 1 as "A1"). The sound or first signal travels down or along the conduit to the end or obstruction and is reflected back along the conduit. The reflected sound may be considered a second signal A2 (illustrated in FIG. 1 as "A2"). As previously mentioned, a feature of the conduit response is the time required by sound to travel from one end of the system to the opposed end. This delay may mean that the sound sensor positioned at one end of the conduit receives the first signal coming from the flow generator, and then some time later receives the same sound filtered by the conduit as reflected second signal A2 (and potentially any other system attached, like human respiratory system, when the conduit is intubated within a patient). This may mean that the part of the IRF associated with the reflection from the conduit appears after a delay. The delay may be considered approximately equal to the time taken for sound to travel from the sound source to the patient end or to an obstruction of the conduit, be reflected, and travel back again.

When the system is loss-prone, given the length of the conduit, the part of the IRF associated with the response at the flow generator will decay to a negligible amount by the time the reflection response has begun. When this occurs, the response due to obstruction may be completely separated from the flow generator response in the system IRF.

For example, a generated noise or noise source can be produced by a flow generator running at a constant speed during the time period of the sound sensor's measurement. This noise may be described as "cyclostationary". That is, it is stationary random, and periodic in its statistics. This means that the noise source and system response may be "smeared" across all measured times because at any point in time, the system output is a function of all previous values of the input signal and system response.

A potential methodology and system for separating the obstruction reflection in some embodiments from this convolutive mixture of sound may be performed in accordance with the operations described above with regard to Equations 1, 2, 3 and 4.

The separation of the obstruction reflection may be assisted by the fact that the cepstrum of white noise (a signal with a flat spectrum) is short such that it appears only at the beginning of the cepstrum, but as has already been shown, the part of the system IRF containing the obstruction reflection appears after the time delay caused by the tube. This can mean that if the flow generator noise is white enough the obstruction reflection response will be separated from both the noise and response of the flow generator.

Thus, in some embodiments, a continuous sound of the operation of the flow generator may be taken as the sound impulse (s1(t)) to the system by considering an arbitrary point in time during the continuous sound to be the sound impulse. In such a case, the sound generator would not need to produce periods of silence or reduced sound before and after a relative increase in sound to thereby produce an actual momentary sound impulse. However, in some embodiments such a momentary sound impulse may be generated by modulation of the control signals to the flow generator or sound source such as by setting low or no speed, followed by an instantaneous high speed and then followed by a return to the low or no speed. Other methods of implementing a momentary sound impulse may also be implemented. For example, a speaker may be used to generate an acoustic sound pulse or chirp. Such a sound pulse may even be a broad spectrum impulse.

Figure 3:
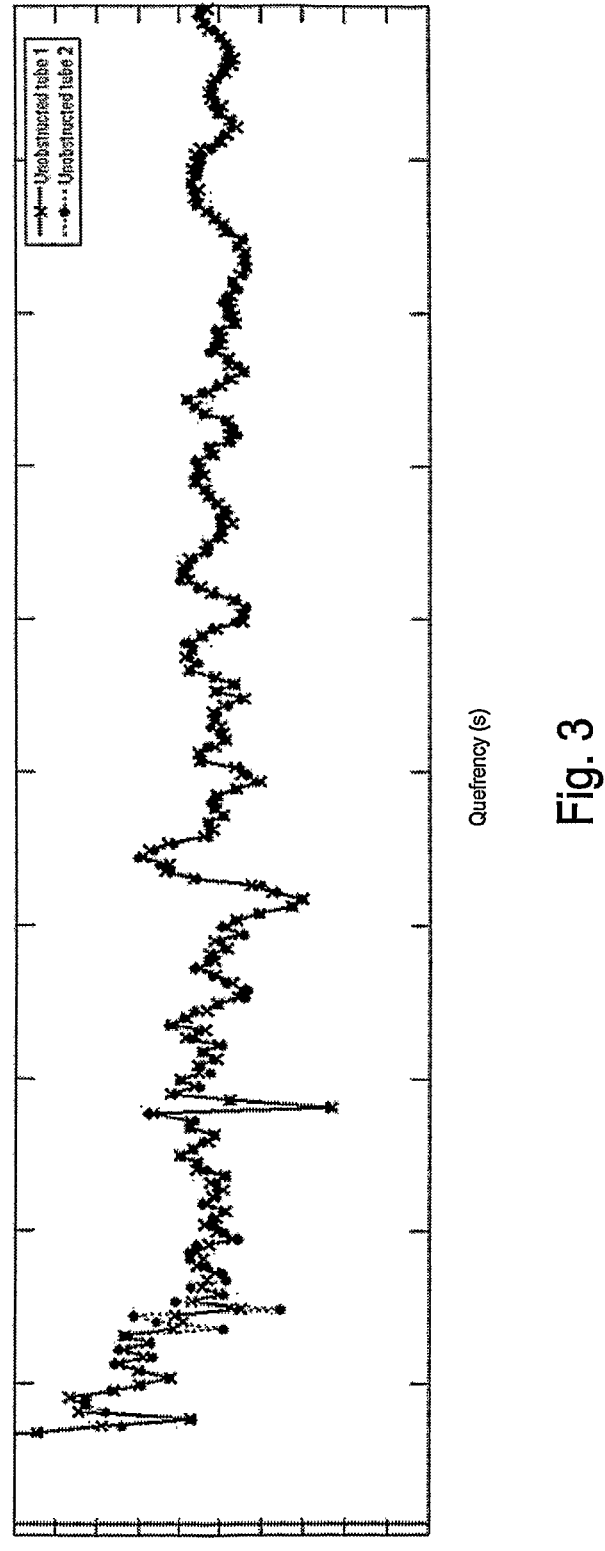
FIG. 3 is a graph of cepstrum data from two sound waves measured from an unobstructed respiratory treatment conduit in accordance with some embodiments of the technology.
Figure 4:
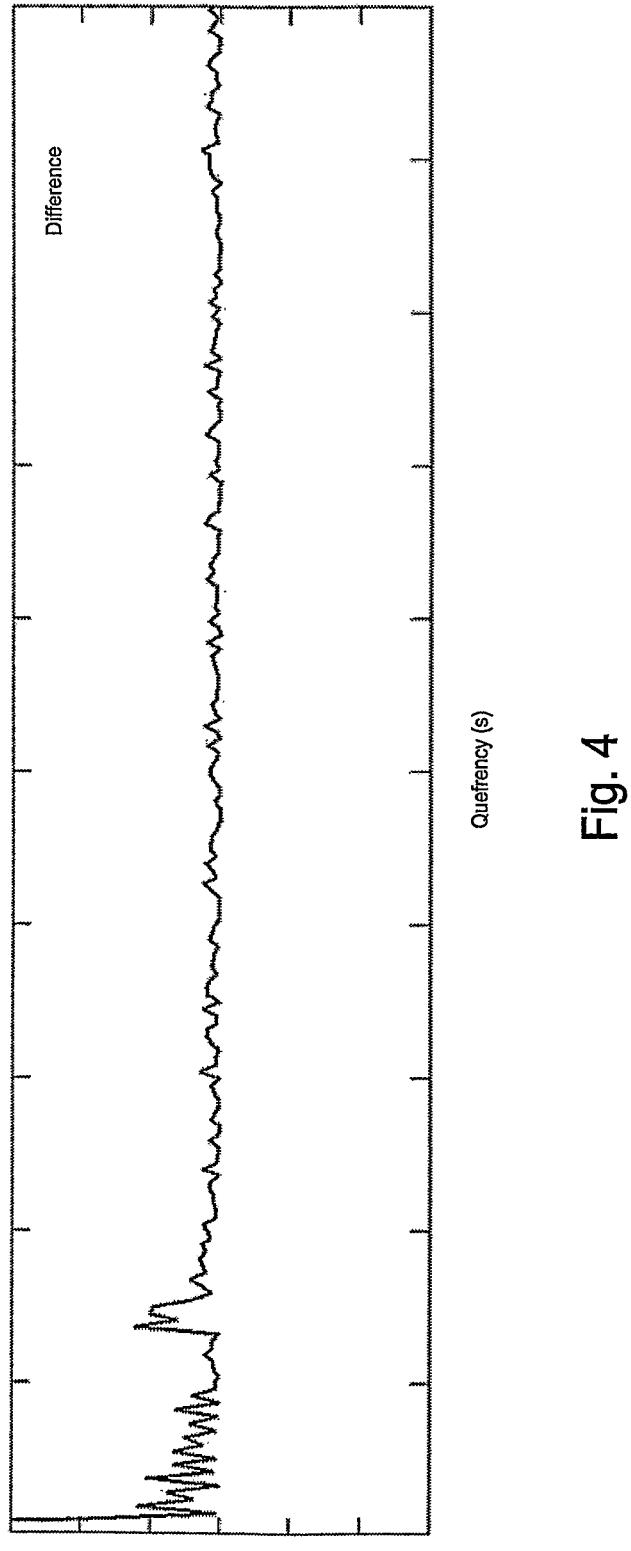
FIG. 4 is a graph of the difference of the cepstrum data of the two sound waves of FIG. 3.

FIGS. 3 through 6 show graphs illustrating an analysis of sound data from a microphone to detect a presence of obstruction based on the cepstrum methodology as previously described. In FIG. 3, data from two distinct sound measurement tests are plotted on a common axis. Sound can be measured such that samples of the microphone signal may be collected or recorded from a chosen or controlled time zero until a sufficient period of time has lapsed to permit the sound to traverse the conduit to the patient end and return to the microphone. In both cases illustrated in FIG. 3, the conduit subject to the measurement process was unobstructed. The measurement samples or sound data from the microphone in each test was subjected to the operations described by equations 1, 2, 3 and 4 previously mentioned and then plotted. In FIG. 4, the difference or magnitude of the difference from the data of the two plots. Such a difference or magnitude may optionally be determined on a sample-by-sample basis as the absolute value of the difference between the sound data of the two tests. The approximately flat line having no significant samples may be taken as a representation of an absence of obstruction along the conduit.

Figure 5:
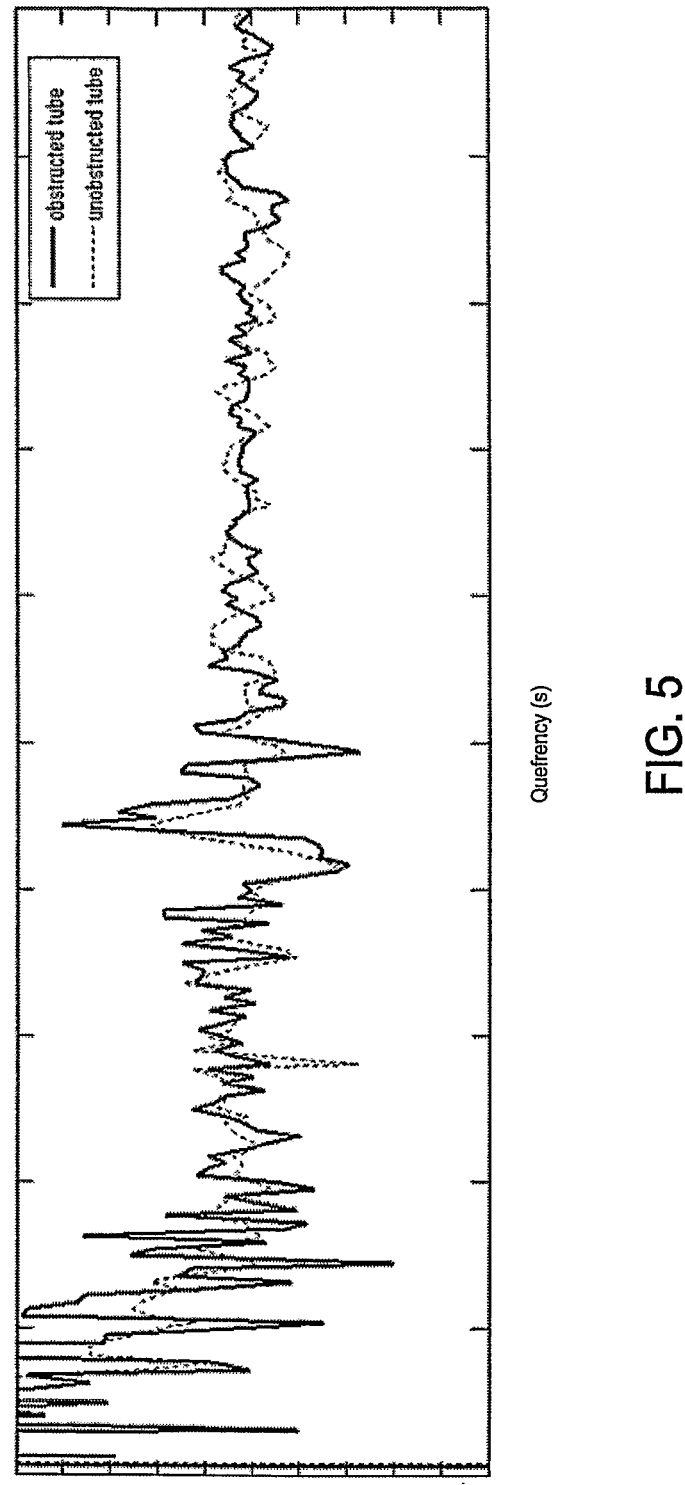
FIG. 5 is a graph of cepstrum data from two sound waves taken from a common respiratory treatment conduit with and without obstruction determined in accordance with some embodiments of the technology.
Figure 6:
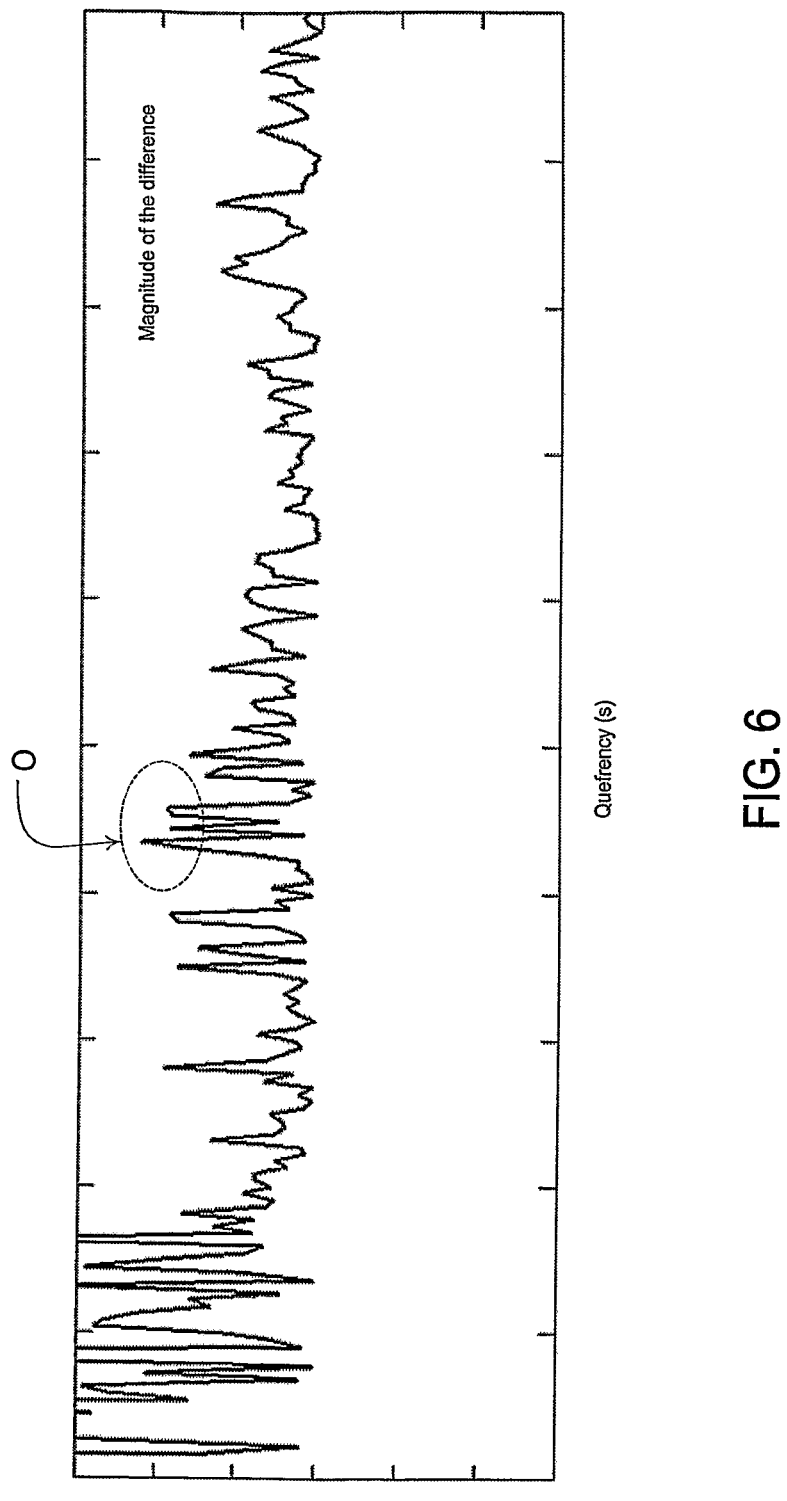
FIG. 6 is a graph of a magnitude of the difference in the cepstrum data from the two sound waves of FIG. 5.

In FIG. 4, data from two distinct sound measurement tests are again plotted on a common axis. In one case the conduit subject to the measurement process was unobstructed and in the other case the conduit of the measurement process was obstructed. The sound data from the microphone in each test was subjected to the operations described by equations 1, 2, 3 and 4 previously mentioned and then plotted. In FIG. 5, the difference or magnitude of the difference from the data of the two plots was then determined on a sample-by-sample basis and plotted. The presence of any significant difference in one or more samples (e.g., one or more values in excess of a threshold at a point along the plot) may be representative of a presence of obstruction or obstructions along the conduit. Such a determination may be made by scanning and assessing the samples of the difference data. Moreover, the magnitude of the value of a particular difference point along the plot of the data may be representative of the extent of the obstruction. Still further, the position of a point along the plot may be assessed as a position of obstruction along the conduit given that the cepstrum data is a function of seconds as follows:

$$\text{Length from sound sensor} = (T_s \times C)/2$$

Where:

$T_s$ is a time position of a significant sample in seconds; and C is the speed of sound.

It will be understood that this calculation may be adjusted to account for the distance from the microphone to the ventilator end of the tested conduit or endotracheal tube.

In an apparatus configured with such a methodology, a pre-measuring process may optionally be performed by the apparatus with a known non-obstructed tube when it is first connected to the apparatus before or at initial use with a patient. Alternatively, data from such a process may be pre-stored based on standard equipment configurations and operational settings. The pre-stored data may then be selected by the user of the apparatus for comparison with new test data. Then, when subsequent tests are made during patient treatment by the apparatus at common ventilator operation settings as the pre-measuring process, the subsequent test data may be used for comparison with the prior data to detect the obstruction and generate associated obstruction information.

While a simple graph like the ones displayed in FIGS. 3 to 6 may be generated by the apparatus to indicate obstruction information, in some embodiments, more detailed reports of the obstruction information may be output to a display device of a detection apparatus or electronically transferred to another apparatus for display on the other apparatus (e.g., a computer or respiratory treatment apparatus). For example, the report may include information identifying (1) whether or not obstruction exists in the endotracheal tube, (2) where an obstruction is located in units of distance from either the microphone, ventilator end and/or the patient end of the endotracheal tube, (3) an extent of obstruction such as a percentage or other measure of the cross section that is blocked by the obstruction or still remaining open. The detector may even trigger a warning message and/or alarm in the event of the detection of a substantial obstruction, such that it may recommend or warn of the need of replacement or cleaning of a current endotracheal tube in use. Thus, a controller of such an apparatus may optionally include a display device such as one or more warning lights (e.g., one or more light emitting diodes). The display device may also be implemented as a display screen such as an LCD. Activation of the detector such as to initiate a pre-measuring process, select pre-measured tube data, initiate an obstruction measuring process, etc. may be performed in conjunction with a user interface such as input switches that operate the controller or processor of the detection apparatus.

Figure 7:
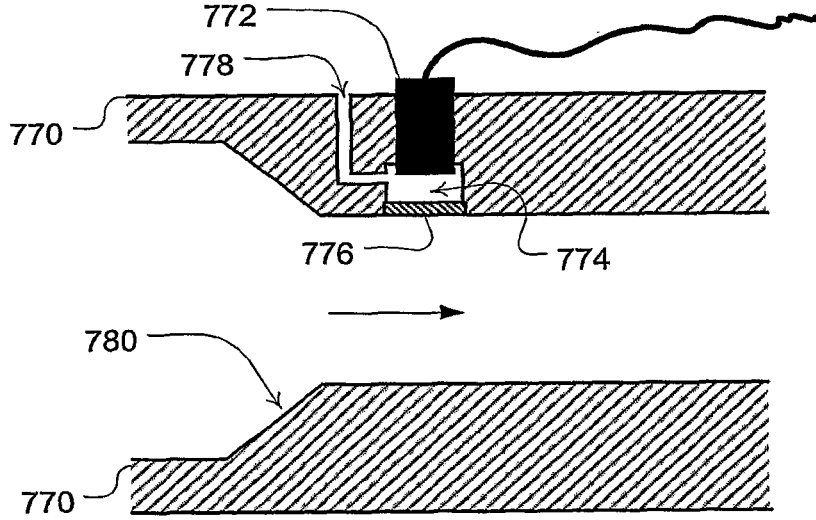
FIG. 7 is a cross sectional view of an embodiment of a sound sensor in a conduit embodiment of the present technology.
Figure 8:
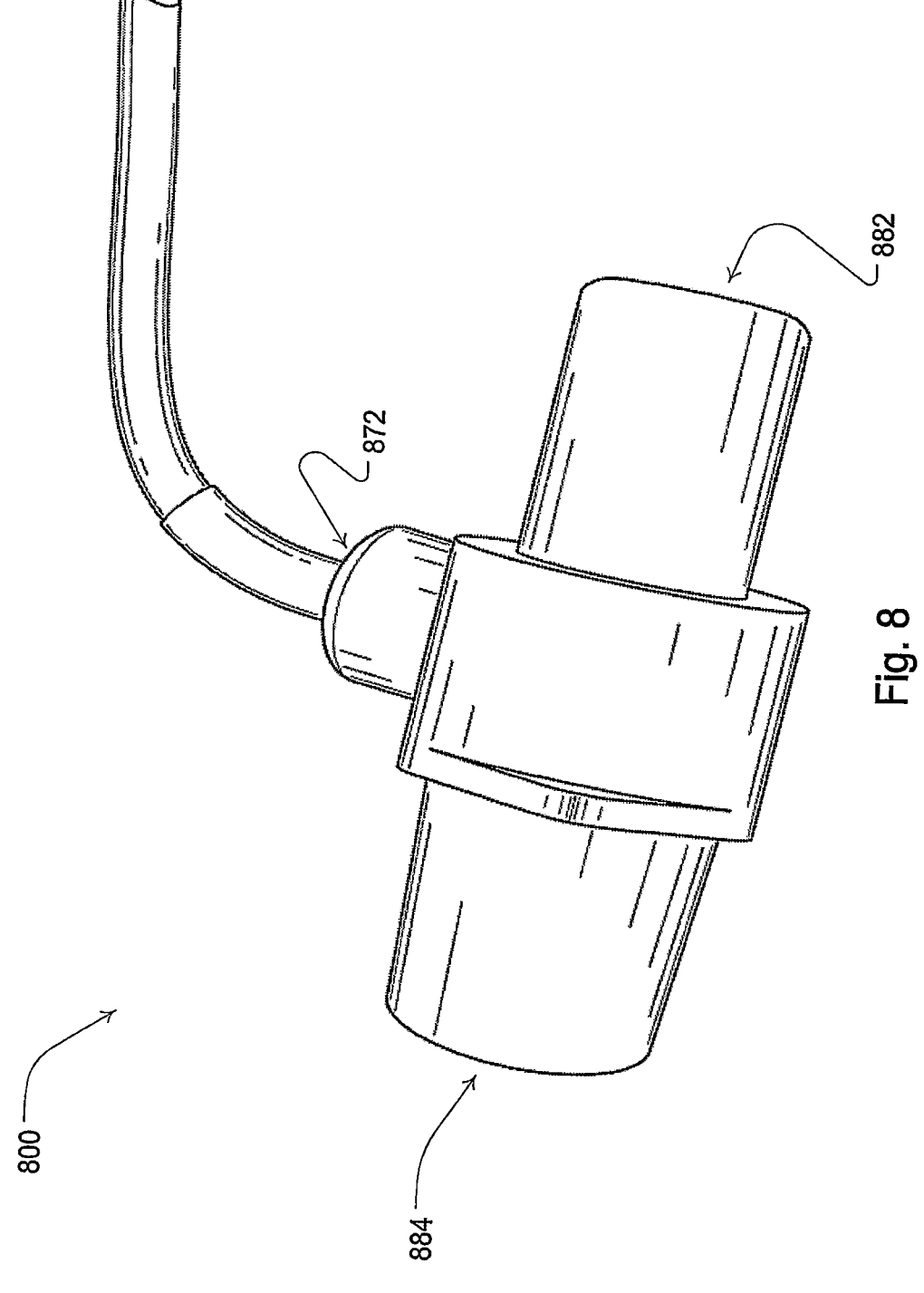
FIG. 8 is an perspective view of an embodiment of a respiratory treatment conduit coupler with a sound sensor of the present technology.

In some embodiments of the technology, the sound sensor may be integrated with a respiratory treatment apparatus conduit (e.g., an endotracheal tube or ventilator supply conduit) or implemented as part of a conduit coupler between conduits. For example, a microphone may be implemented as illustrated in FIGS. 7 and 8. FIG. 7 shows a cross sectional view of a sound sensor integrated into a conduit or coupler. In this example, the microphone 772 is installed into a microphone chamber 774 that is formed within a wall 770. The chamber facilitates the capture of sound from an internal gas flow channel of the conduit. In the embodiment, the wall 770 may serve as a barrier for the flow of gas within the channel of the conduit or coupler. Optionally, a chamber barrier, such as a sound conducting membrane, may separate the gas channel of the conduit and the sound sensor. Such a barrier may serve to protect the microphone. As further illustrated in FIG. 7, the wall may also include a vent 778 adapted to permit the microphone chamber to equalize with ambient pressure. Optionally, the channel of the conduit may include a bevel 780 surface, such as the one illustrated with the conic cross-section shown in FIG. 7. Such a surface may improve acoustic properties of the conduit in its use as a wave guide.

Figure 9:
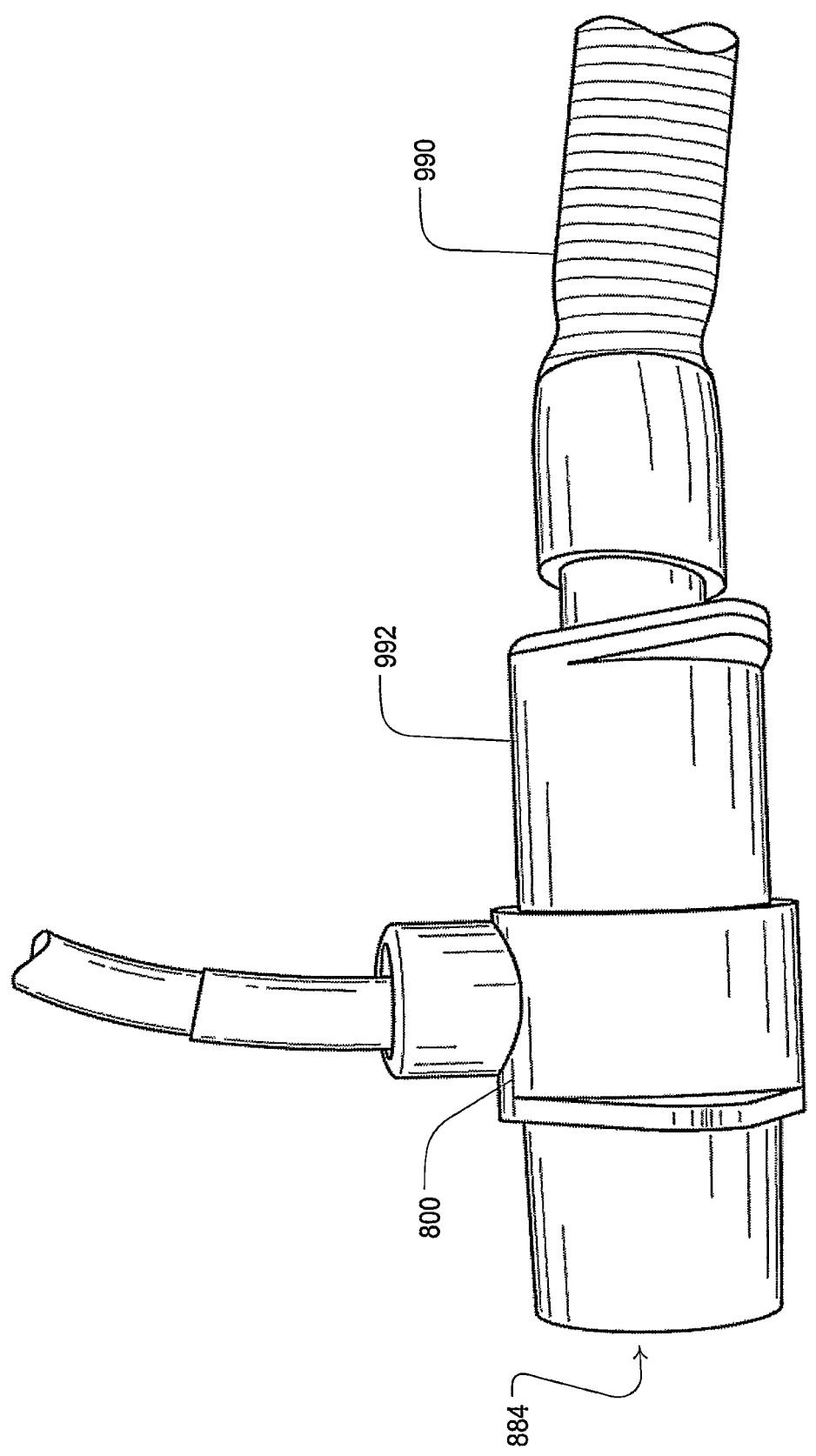
FIG. 9 is an perspective view of the embodiment of the coupler of FIG. 8 fitted with an endotracheal tube.
Figure 10:
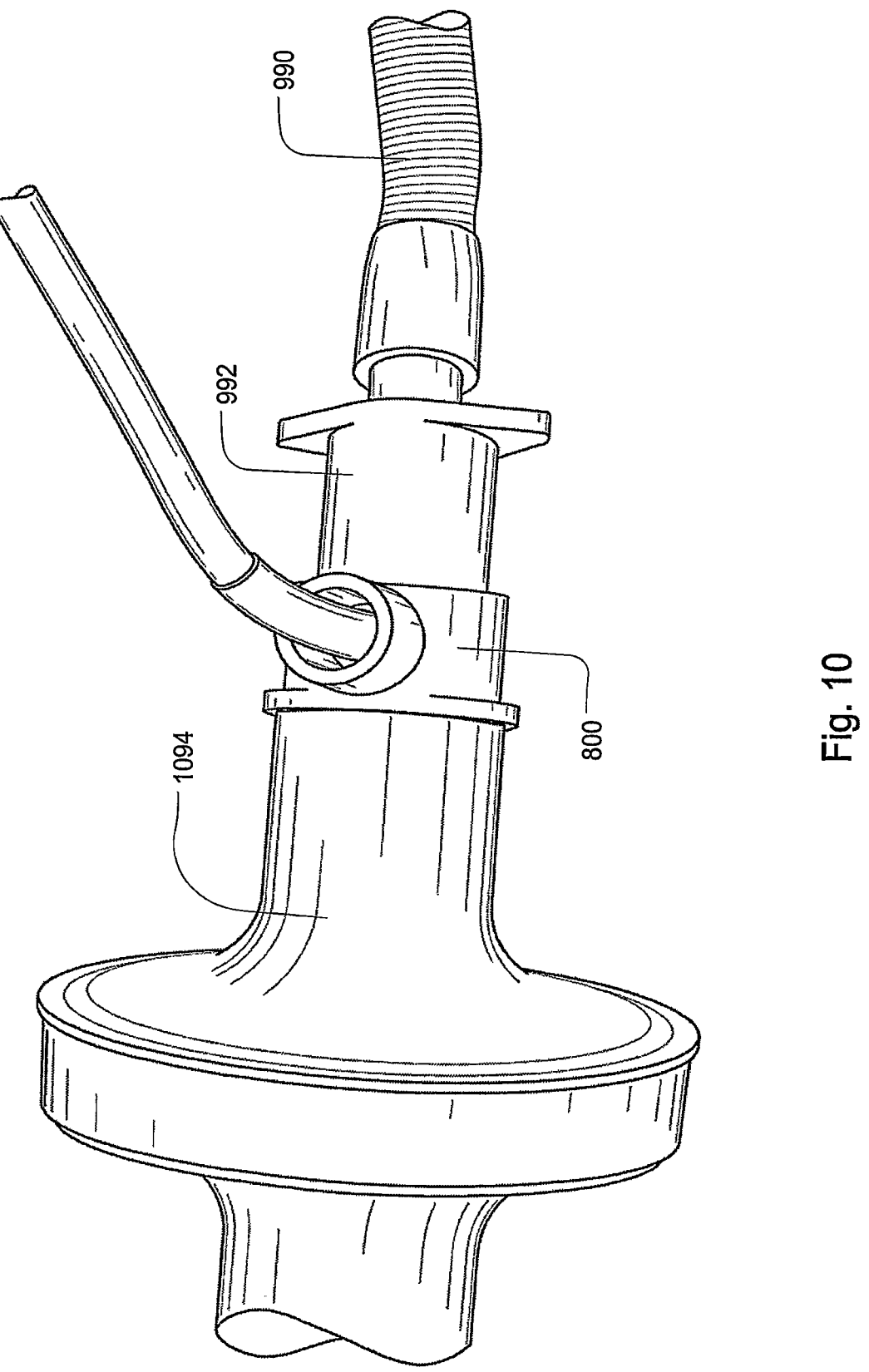
FIG. 10 is an perspective view of the embodiment of the coupler of FIG. 9 also fitted with a flow generator supply conduit.

FIGS. 8, 9 and 10 illustrate an example conduit coupler 800 as previously mentioned for an endotracheal tube. The coupler 800 includes an endotracheal tube mount end 882 and a ventilator supply tube mount end 884. In this embodiment, the ends are sized for connection with either the ventilator supply tube or the endotracheal tube or suitable adapters for the tubes. For example, the tubes may be held in connection with the coupler and/or adapters by interference fit. The sound sensor 872 may optionally be integrated or installed within or into the coupler as described with respect to FIG. 7. In FIG. 9, the coupler 800 is optionally connected with an endotracheal tube 990 via an adapter 992. Such an adapter includes a gas channel to permit gas and sound transfer between the coupler and the tube. In FIG. 10, the coupler 800 is connected with a ventilator supply tube 1094.

Figure 11:
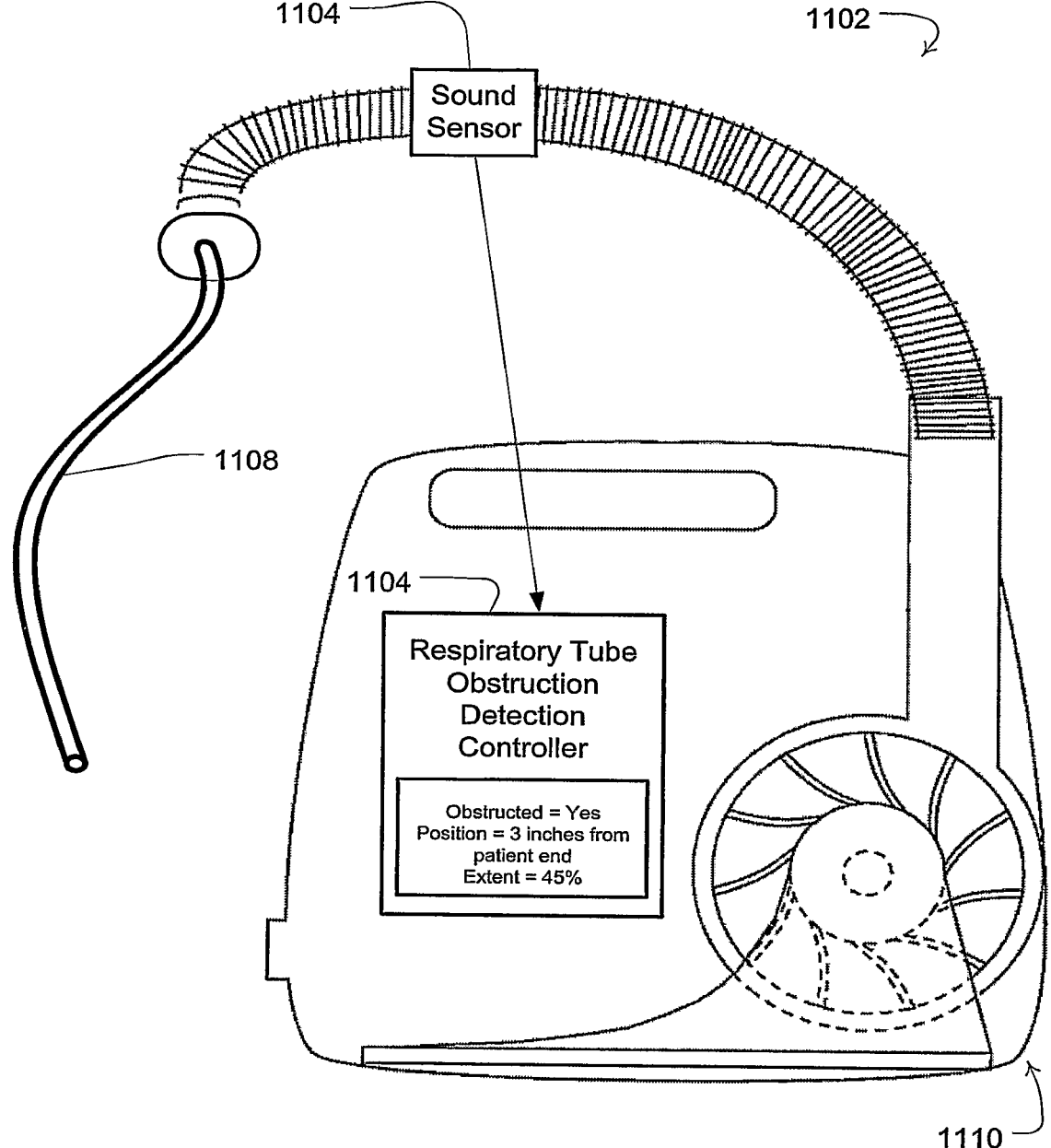
FIG. 11 is an illustration of example components of a respiratory treatment apparatus configured with obstruction detection in accordance with some embodiments of the present technology.

In reference to the embodiment of FIG. 1, the obstruction detection apparatus 102 may serve as a detector that is used with, but structurally independent of, a respiratory treatment apparatus. In such an embodiment, the common operational settings of the flow generator used for the tests may be manually set by a clinician. However, in some embodiments, the obstruction detection apparatus 1102 may be integrated with or be a component of a respiratory treatment apparatus, such as in the embodiment illustrated in FIG. 11. In such a device, the controller 1106 that controls the delivery of pressure or ventilation treatment of a patient via a flow generator, may also serve as the tube obstruction detection controller. In such an embodiment, the sound sensor 1104 may be directly coupled with the controller 1106 of the respiratory treatment apparatus for the acoustic measurement of obstruction of an endotracheal tube 1108. Such a device may include a pressure sensor, such as a pressure transducer to measure the pressure generated by the blower 1100 and generate a pressure signal p(t) indicative of the measurements of pressure. It may also optionally include a flow sensor. Based on flow f(t) and pressure p(t) signals, the controller 1106 with a processor may generate blower control signals.

For example, the controller may generate a desired pressure set point and servo-control the blower to meet the set point by comparing the set point with the measured condition of the pressure sensor. Thus, the controller 404 may make controlled changes to the pressure delivered to the patient interface by the blower 102. Optionally, it may include a speed sensor so as to control the blower to a particular RPM setting. In this regard, in addition to automated respiratory treatment, the obstruction measuring processes of the apparatus may be automated so as to directly control particular settings of the blower during the acoustic measuring as previously described. In this manner it may maintain common operational settings during tube obstruction tests.

Figure 12:
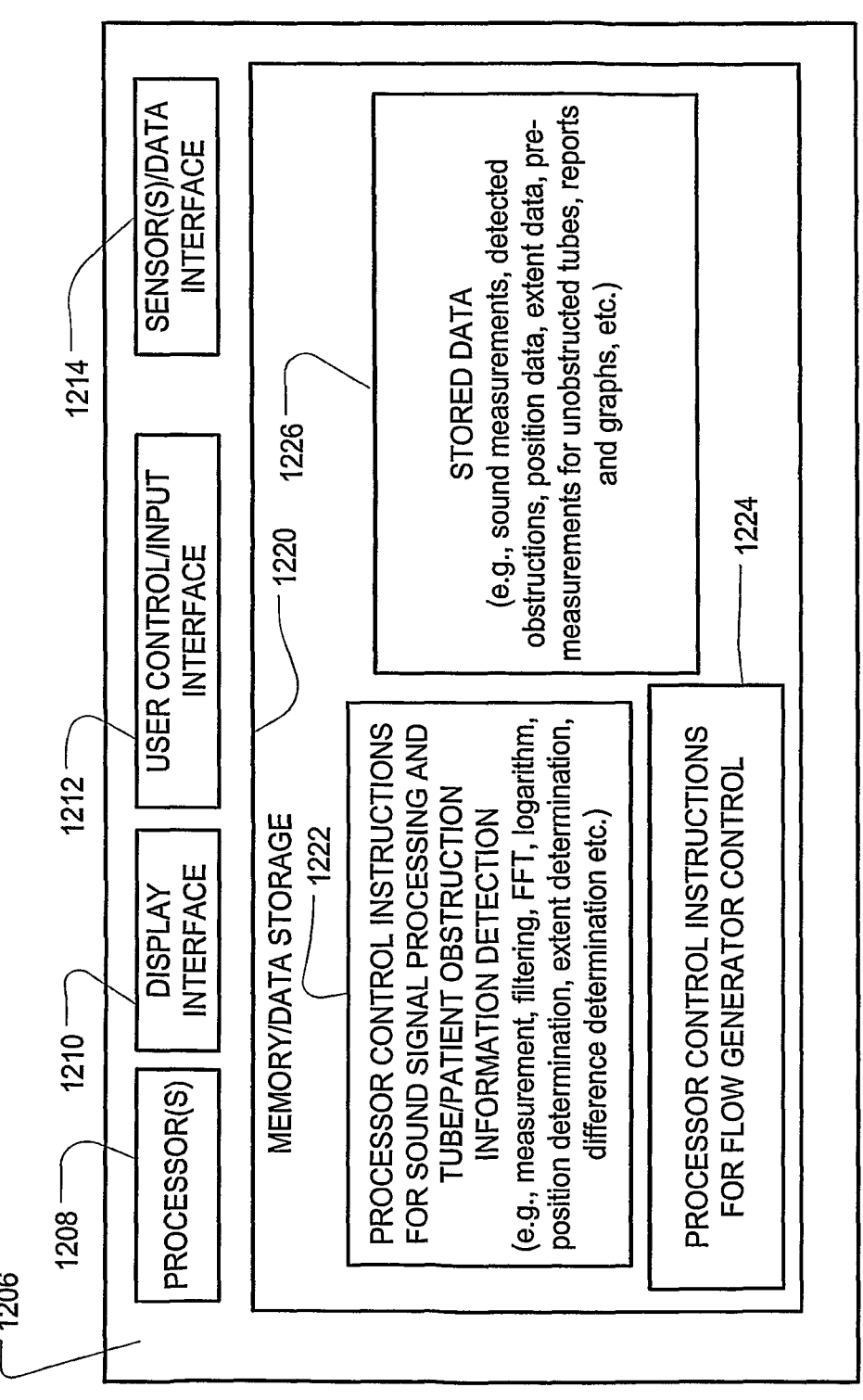
FIG. 12 illustrates a block diagram of an example controller architecture of the present technology with conduit obstruction detection technology.

An example architecture for a conduit obstruction detection controller 1206 is illustrated in the block diagram of FIG. 12. In the illustration, the controller may be implemented by one or more programmable processors 1208. The device may also include a display interface 1210 to output data for a user interface or display device as previously discussed (e.g., detected conduit obstruction information, etc.) to a display such as on a monitor, LCD panel, touch screen, etc. A user control/input interface 1212, for example, for a keyboard, touch panel, control buttons, mouse etc. may also be included as previously discussed and for inputting data, or otherwise activating or operating the methodologies described herein. The device may also include a sensor or data interface 1214, such as a bus, for receiving/transmitting data such as programming instructions, settings data, sound data, microphone sound samples, acoustic measurement data, obstruction information, etc.

The controller also includes memory/data storage components 1220 containing control instructions and data of the aforementioned methodologies. For example, at 1222, they may include stored processor control instructions for sound signal processing and tube obstruction information detection, such as, measurement, filtering, FFT, logarithm, position determination, extent determination, difference determination etc. At 1224, these may also include stored processor control instructions for flow generator control, such as respiratory treatment control based on feedback processing and measuring process settings adjustment, etc. Finally, they may also include stored data at 1126 for the methodologies such as sound measurements, detected obstructions, position data, extent data, pre-measurements for unobstructed tubes, reports and graphs, etc.

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

While the conduit obstruction detection technology has been described in several embodiments, it is to be understood that these embodiments are merely illustrative of the technology. Further modifications may be devised within the spirit and scope of this description.

For example, while an integrated obstruction measuring and reporting device is contemplated by the present technology, the methodology of the components of the device may be shared across multiple components of a system. For example, a measuring device may simply conduct the measuring processes to determine the acoustic data of the conduits and transfer the data to another processing system. The second processing system may in turn analyze the data to determine the obstruction information as previously discussed. The second processing system may then indicate the obstruction as described herein, such as by sending one or more of the described messages, in electronic form for example, back to the measuring or other apparatus for display to warn the clinician or physician.

Similarly, while the technology contemplates embodiments where data from only a single microphone may be implemented to detect conduit obstruction, in some embodiments of the technology additional microphones may be implemented. Moreover, while the technology contemplates embodiments where the noise or sound of the system that serves as the sound impulse is the sound generated by a flow generator operating at one or more chosen blower settings, in some embodiments, a speaker or horn driver may be implemented to generate the sound impulse in the conduit that is recorded by the sound sensor. Moreover, while some embodiments are implemented to compare cepstrum data from known unobstructed tubes with the cepstrum data of obstructed tubes, additional comparisons may be made between tubes with varying degrees of obstruction so that the changing nature of an obstruction may be tracked and indicated to a user.

In some embodiments, the technology may also be implemented to detect a presence of obstruction of the respiratory pathways of the patient's respiratory system, such as closure or partial closure (e.g., narrowing associated with obstructive apnea). For example, based on the cepstrum analysis and determination of a distance from the microphone as previously described, a detection of a significant value in the cepstrum difference data may be indicative of obstruction or partial obstruction beyond the length of any respiratory treatment conduit, endotracheal tube or mask. In such a case, the data may be taken as an indication of obstruction of the patient's respiratory pathways. In such an embodiment, a period of sound data may be recorded so as to collect sufficient data for sound to reflect back from beyond the end of the conduit or mask of the respiratory apparatus. By conducting the aforementioned cepstrum analysis and difference calculation, a device may then indicate patient obstruction (in addition to or as an alternative to treatment conduit obstruction). Based on one or more significant values in the cepstrum difference data that are associated with a distance beyond the known end of the apparatus conduit, an extent of obstruction (e.g., increase or decrease), presence or absence of obstruction and/or a position of obstruction may then be displayed or output by the detection apparatus in a similar manner as previously described with regard to obstruction of a respiratory treatment conduit. In such a device a pre-measuring process may be implemented to determine cepstrum data for the system when it is known that the respiratory apparatus and patient respiratory system are either unobstructed or otherwise less obstructed so that later analysis of test data may be compared to indicate a change in obstruction (e.g., increase or decrease).

Such an analysis of acoustic reflection data of the patient's respiratory system can serve generally as a test to detect the condition of the patient's respiratory system in addition to a detection of presence of absence of obstruction or partial obstruction. For example, acoustic reflection data may be analyzed to detect lung condition and/or monitor changes in lung condition. For example, an apparatus may be configured to measure the acoustic reflection from the lungs over several days (e.g., once a day) and then compare the data from each to detect changes. Changes may indicate improvements or deterioration in respiratory condition. It may even be compared to templates representing empirically collected and stored reflection data that is associated with certain respiratory related conditions.

In some embodiments where reflection data of particular interest is in the patient's respiratory system, the acoustic response of the patient interface (e.g., tube or mask) may be made so as to reduce the possibility of reflections that result from the mask or conduits. In this way, reflection data may be more readily attributable to the respiratory condition of the patient.

In still further embodiments, reflection data may be analyzed to detect lung or patient characteristics such as lung impedance, rhinometry, whether a humidifier is needed, heart failure via odema and other increases in patient airway resistance.

In some embodiments, the frequency domain may be processed to isolate or emphasize data of interest in detecting a particular condition or system accessory. For example, the process may involve filtering with respect to particular frequencies (e.g., low pass, high pass, band pass, etc.). In this regard, it may be useful to include or exclude certain spectral components such as filtering out spectral components to exclude frequencies not particularly related to a detection of interest. For example, frequencies associated with snoring sounds or leak sounds may be filtered out to assist in mask detection or other patient condition detection. In this regard, information about mask geometry might typically be contained in higher frequency signal components, whereas information about leak and snore and perhaps lung parameters may be more readily seen in lower frequency components of the signal. By way of further example, the process might adjust the sound sampling parameters such as sample rate and record length to suit the particular detection application of interest. For example in order to detect information about a patient's snoring condition (which typically consists of relatively low frequencies) it might be advantageous to implement recording or capturing of sound data during a longer period of time while at the same time the sampling rate may be reduced. In such a case, further filtering out of particular frequencies associated with the motor or impeller of the flow generator may be useful.

B. Accessory Detection

As previously mentioned, apparatus to deliver breathable gas to a patient typically includes a flow generator, an air delivery conduit, and a patient interface. A variety of different forms of patient interface may be used with a given flow generator, for example nasal pillows, nasal mask, nose & mouth mask, full face mask. Furthermore, different forms of air delivery conduit may be used. In order to provide improved control of therapy delivered to the patient interface, it may be advantageous to measure or estimate treatment parameters such as pressure in the mask, and vent flow. In systems using estimation of treatment pressures, knowledge of exactly which mask is being used by a clinician can enhance therapy. For example, known flow generators include a menu system that allows the patient to select the type of peripheral components being used, e.g., by brand, method of delivery, etc. Once the components are selected by a clinician, the flow generator can select appropriate operating parameters of the flow generator that best coordinate with the selected components.

The present technology may provide improvements to known apparatus to facilitate the coordination between the flow generator and the peripheral components based on acoustic detection to distinguish or identify particular components.

A first embodiment of the present technology comprises, a device, a system, an identifier and/or a method for identifying the patient interface device. The patient interface devices may be masks and the tubing for use with respiratory treatment apparatus such as a Continuous Positive Air Pressure systems ("CPAP") or similar systems. This embodiment may detect and identify the length of the tubing connected to such an apparatus or CPAP device, as well as the model of mask connected to the tubing. The technology may also identify the mask and tubing regardless of whether a patient is wearing the mask portion at the time of identification.

The technology may implement analysis of an acoustic signal sensed by a microphone or other similar sensor near, proximal to or at a Flow Generator (herein referred to as "FG"). However, is also possible to replace the microphone with pressure or flow sensors.

This technology includes a proposed analysis method that enables the separation of the response of the acoustic mask reflections from the other system noises and responses, including but not limited to motor or blower noises. This may make it possible to identify differences between different mask's acoustic reflections (usually dictated by mask shapes, configurations and materials) and may permit the identification of different masks without user or patient intervention.

An example method of detecting and identifying the mask may be to compare a measured acoustic reflection response with a predefined or predetermined database of previously measured reflection responses for known masks. Optionally, some criteria would be set to determine appropriate similarity. In one example embodiment, the comparisons may be completed based on the single largest data peak in the cross-correlation between the measured and stored reflection responses such as those represented by quefrency data determined from cepstrum analysis. However, this may be improved by comparisons over several data peaks or alternately, wherein the comparisons are completed on extracted unique sets of wave features.

Alternatively, the same measurement system or methodology may be also used to determine the tube or conduit length, by finding the delay between a sound being received from the FG and its reflection from the mask; the delay may be proportional to the length of the tube. Additionally, changes in tubing diameter may increase or decrease the amplitude of the outputted waveforms and therefore may also be detectable and identifiable. Such an assessment may be made by comparison of current reflection data with prior reflection data. The diameter change may be considered as a proportion of the change in amplitude from the waveforms (i.e., reflection data).

Figure 13:
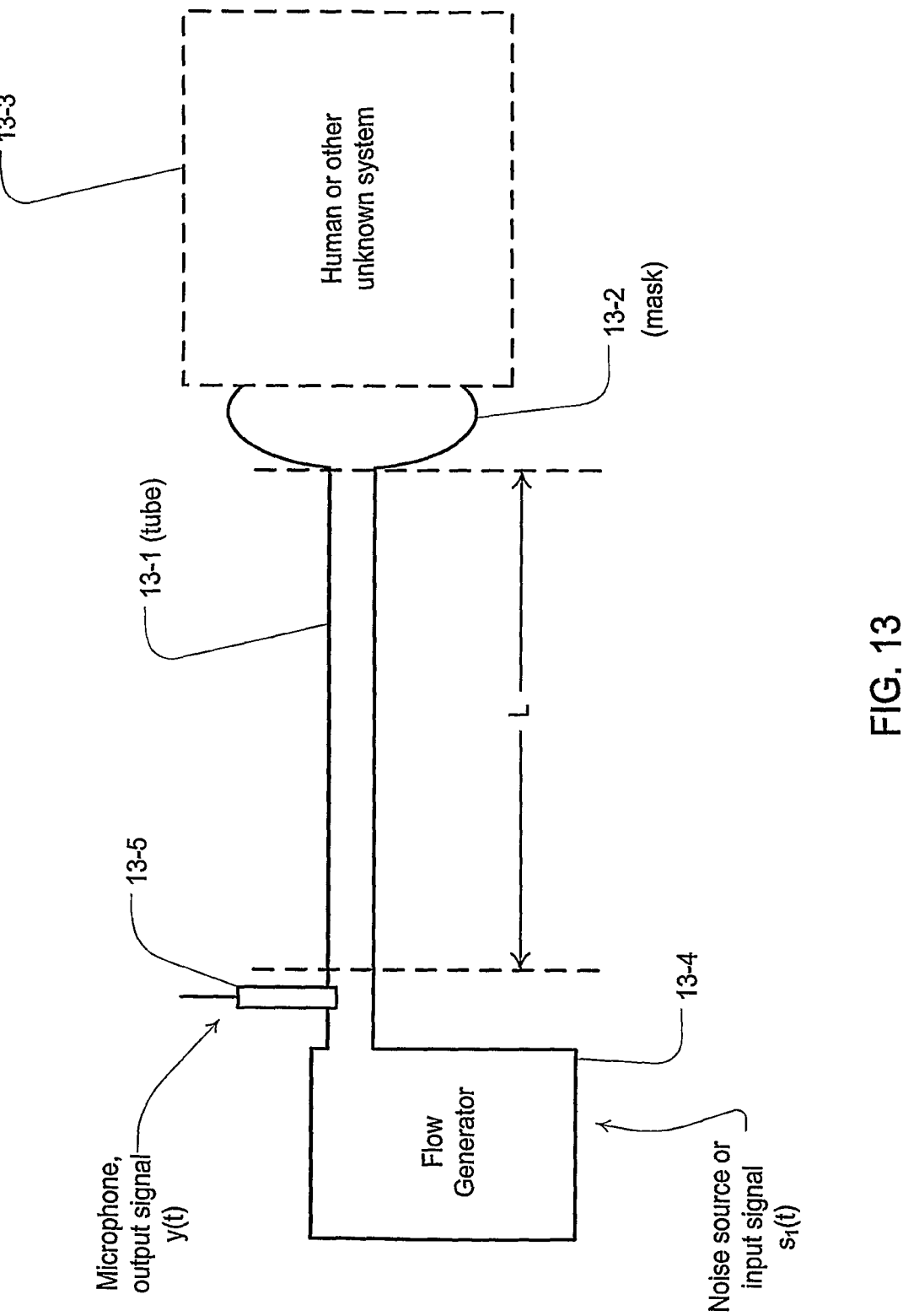
FIG. 13 is a schematic view of a first preferred embodiment of the present invention.

FIG. 13 depicts a schematic view of a further example embodiment of the present technology. The delivery tubing of the FG may be fitted with a small microphone which records the sound pressure in the airpath. The microphone may be directly exposed to the airpath for greater reception of noise or sound, or could also be encapsulated behind a thin layer of flexible membrane material. This membrane may function to protect the microphone from heat and/or humidity.

In this example embodiment as shown in FIG. 13, the tube or tubing 13-1 effectively acts as a wave guide for sound produced by the FG 13-4. Sound is emitted in this embodiment by the FG 13-4 and forms a first signal. The sound or first signal travels down or along the airpath in tubing 13-1 to mask 13-2 and is reflected back along the tubing 13-1 by features in the gas or airpath (which may include the tubing and/or mask) and is called the reflected second signal. A key feature of the tube response is the time required by sound to travel from one end of the system to the opposed end. This delay may mean that the microphone 13-5 positioned at one end of the tube 13-1 receives the first signal coming from the FG 13-4, and then some time latter receives the same signal filtered by the tube 13-1 (reflected second signal), and reflected and filtered by the mask 13-2 (and potentially any other system attached, like human respiratory system, when the mask is fitted to a patient). This may mean that the part of the IRF associated with the reflection from the end of the tube 13-1 appears after a delay. The delay may be equal to the time taken for sound to travel from the sound source to the end of the tube, be reflected, and travel back again.

Figure 14:
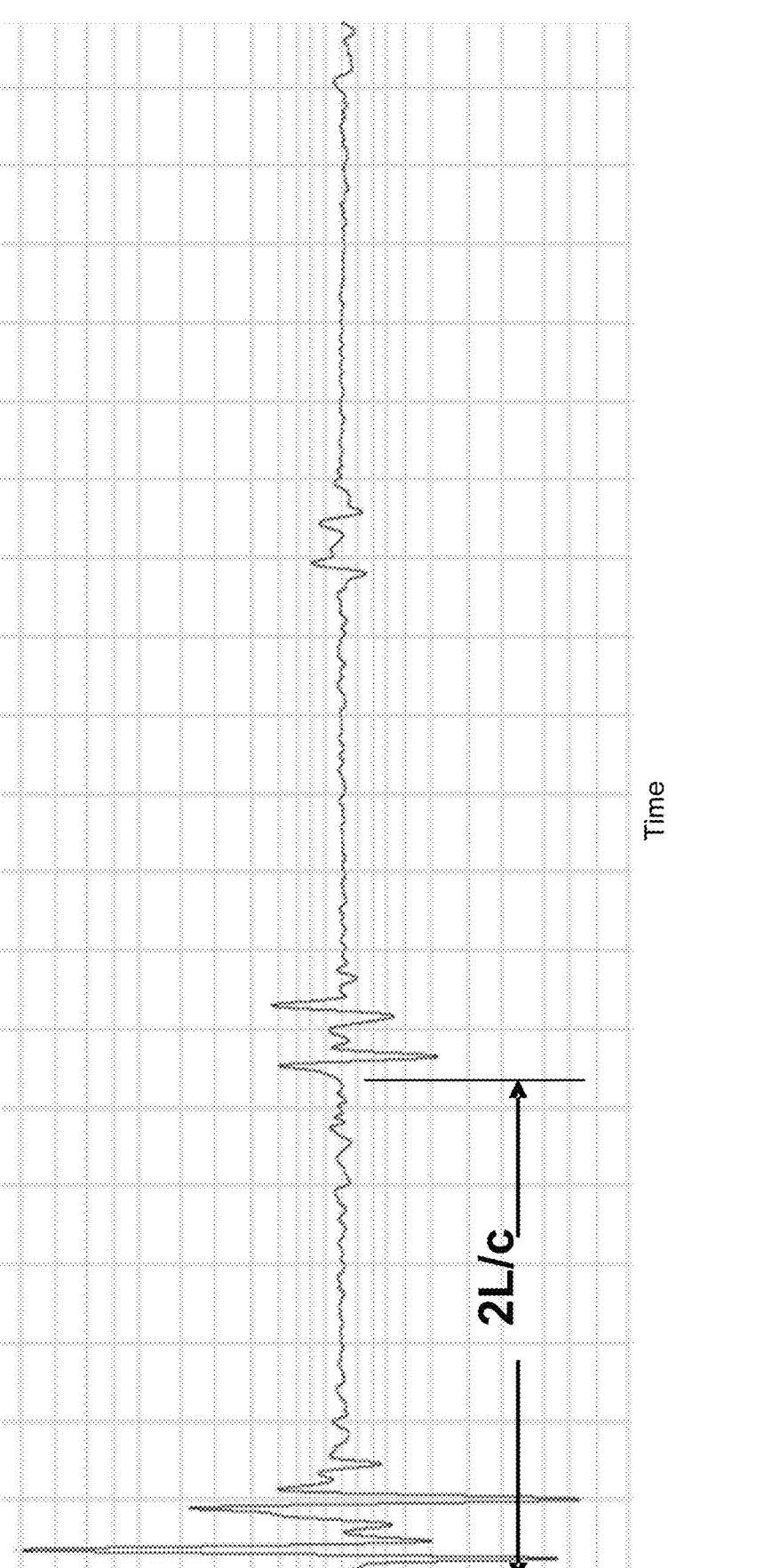
FIG. 14 is a graph demonstrating an example of an Impulse Response Function as per the first preferred embodiment.

Another feature of the system IRF is that because the system is loss-prone, provided the tube is long enough, the part of the IRF associated with the response at the FG will decay to a negligible amount by the time the mask reflection response has begun. If this is the case, then the mask response may be completely separated from the FG response in the system IRF. As an example, FIG. 14 shows a sound measurement of one such system IRF. Although of course in practice an imperfect impulse is used to excite the system, it still shows that the mask reflection appears well separated from the FG response.

Generally, the time at which the mask reflection appears in the IRF should be 2L/c plus any additional delay between the source and the microphone (wherein 'L' is the length of the tube, and 'c' is the speed of sound in the tube). For practical purposes, we generally can ignore the additional delay and approximate time zero when the microphone first responds to the impulse. This may generally allow the mask reflection to occur at a time identified by 2L/c. Thus, the data associated with the time of the mask reflection may be assessed in the identification of which mask is connected to the flow generator by comparing this data with known mask response data.

The example of IRF depicted in FIG. 14, illustrated the example system excited by an impulse which may be a noise including the motor/blower of the flow generator. Alternatively, it may be a sound impulse of short duration from a speaker. In the methodology of this embodiment, an apparatus separates the reflected noise or sound signal (for example the noise reflected from the mask or tubing conduits) from the other system artifacts (including but not limited to the reflections from the FG), which may be implemented by analysis of the measured sound signal (e.g., by examination of position and amplitude of data of either the sound signal or the quefrency data from the cepstrum analysis associated with equations 1, 2, 3 and 4 previously described).

However, the generated noise may be either transient, or stationary random. The latter case may make it more difficult to distinguish the reflection response from the system artifacts. Nevertheless, the present technology may still serve to resolve the IRF despite the type of impulse.

Thus, in some embodiments, the generated noise or noise source can be produced by a flow generator FG running at a constant speed so as to produce the smeared cyclostationary noise as previously discussed. Thus, the cepstrum analysis methodology may be implemented for separating the mask reflection from this convolutive mixture. However, the accessory identification system may be able to determine and identify masks (and/or tubing) without separation of the noise and response.

Figure 15:
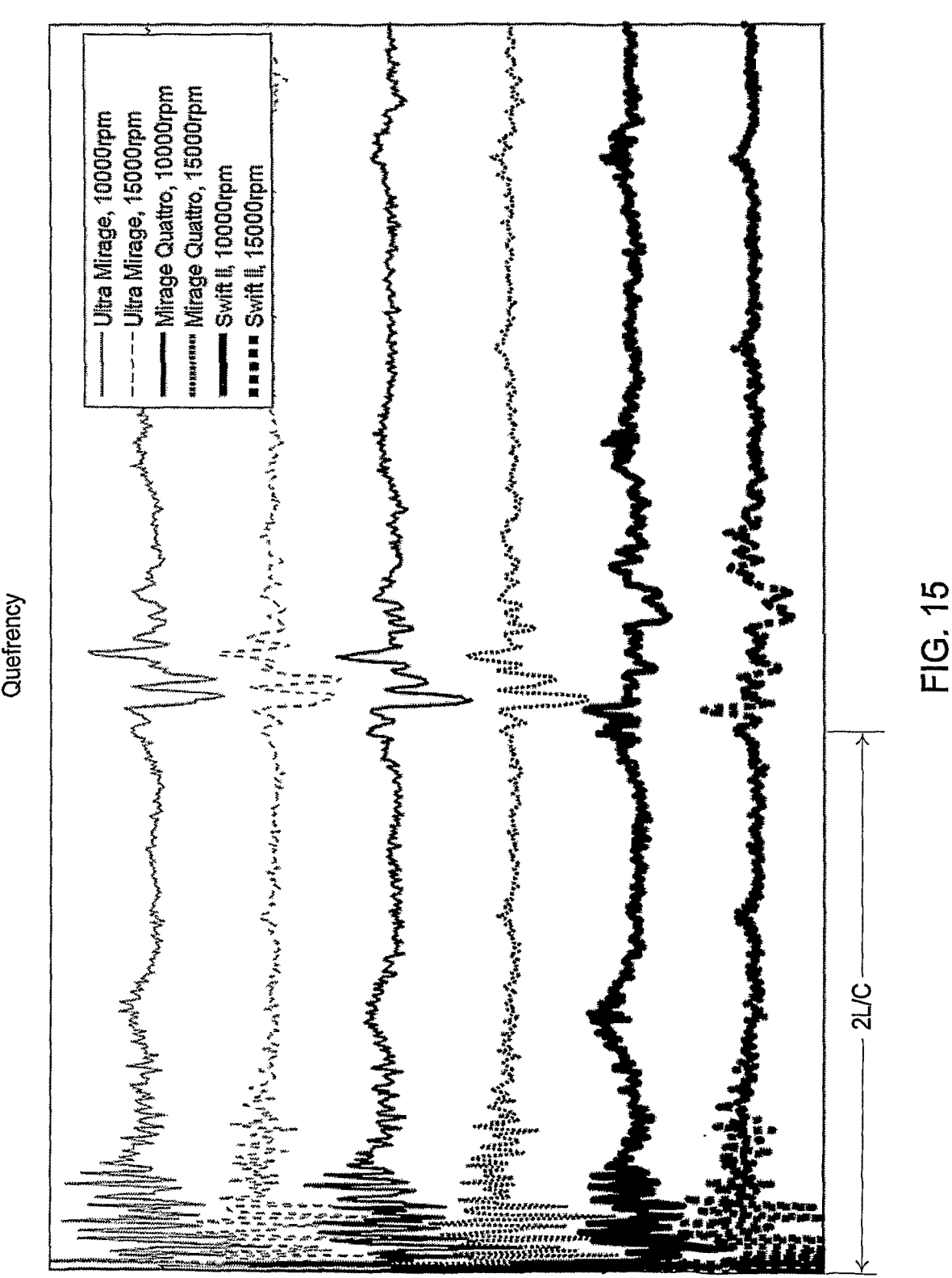
FIG. 15 is a further graph demonstrating various cepstra of various example masks at various flow generator speeds.

FIG. 15 depicts various example cepstra from measurements of a flow generator FG system, such as the system of FIG. 13, that has been used with three different masks. Each respective mask in this example was tested at two different operational speeds of the flow generator, namely 10 krpm, and 15 krpm. Although these speeds were used in the examples, the methodology may be implemented with other speeds particularly if the noise generated and reflection is detectable by the microphone.

Figure 16:
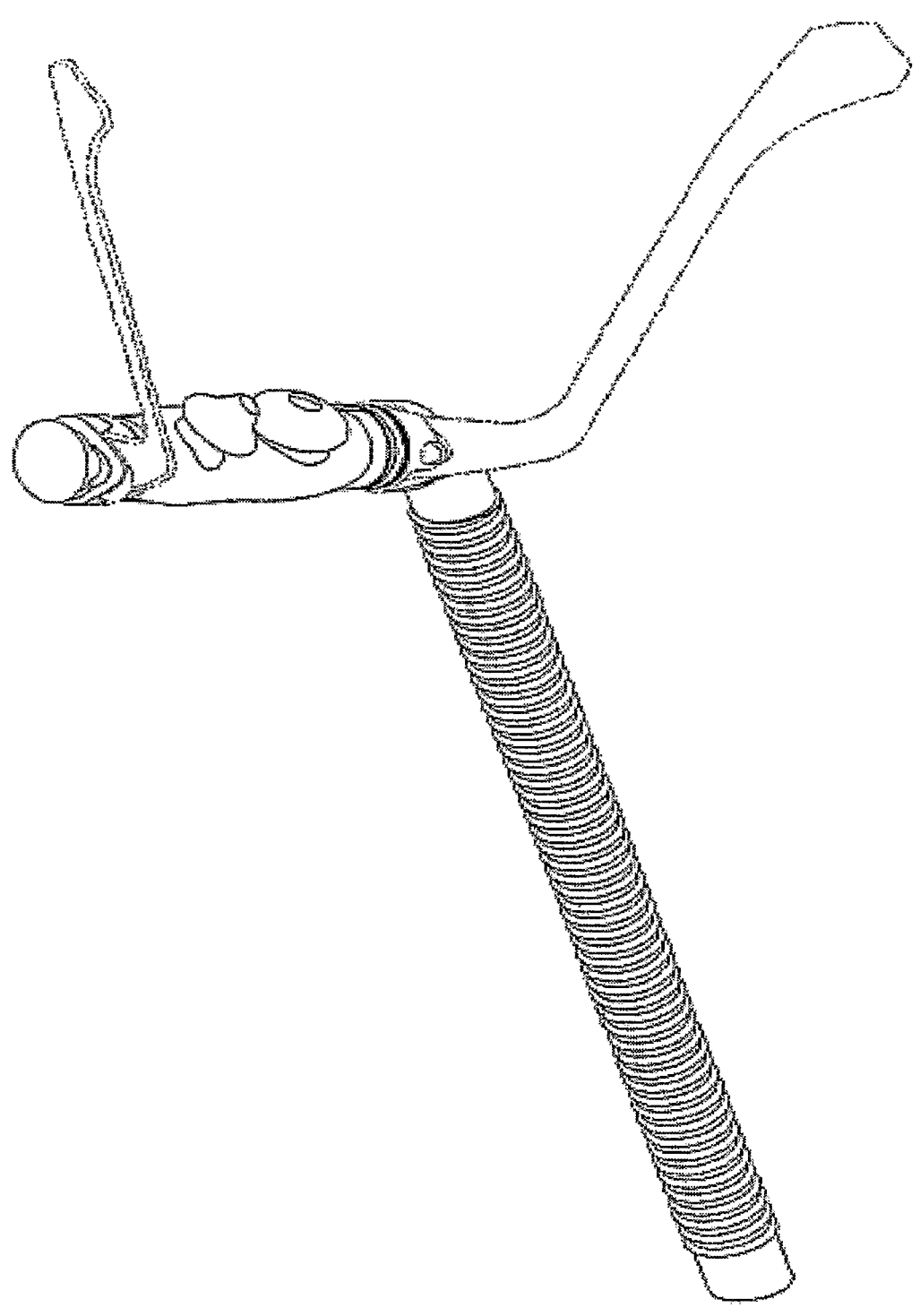
FIG. 16 depict a first example of a mask for use with an example embodiment.
Figure 17:
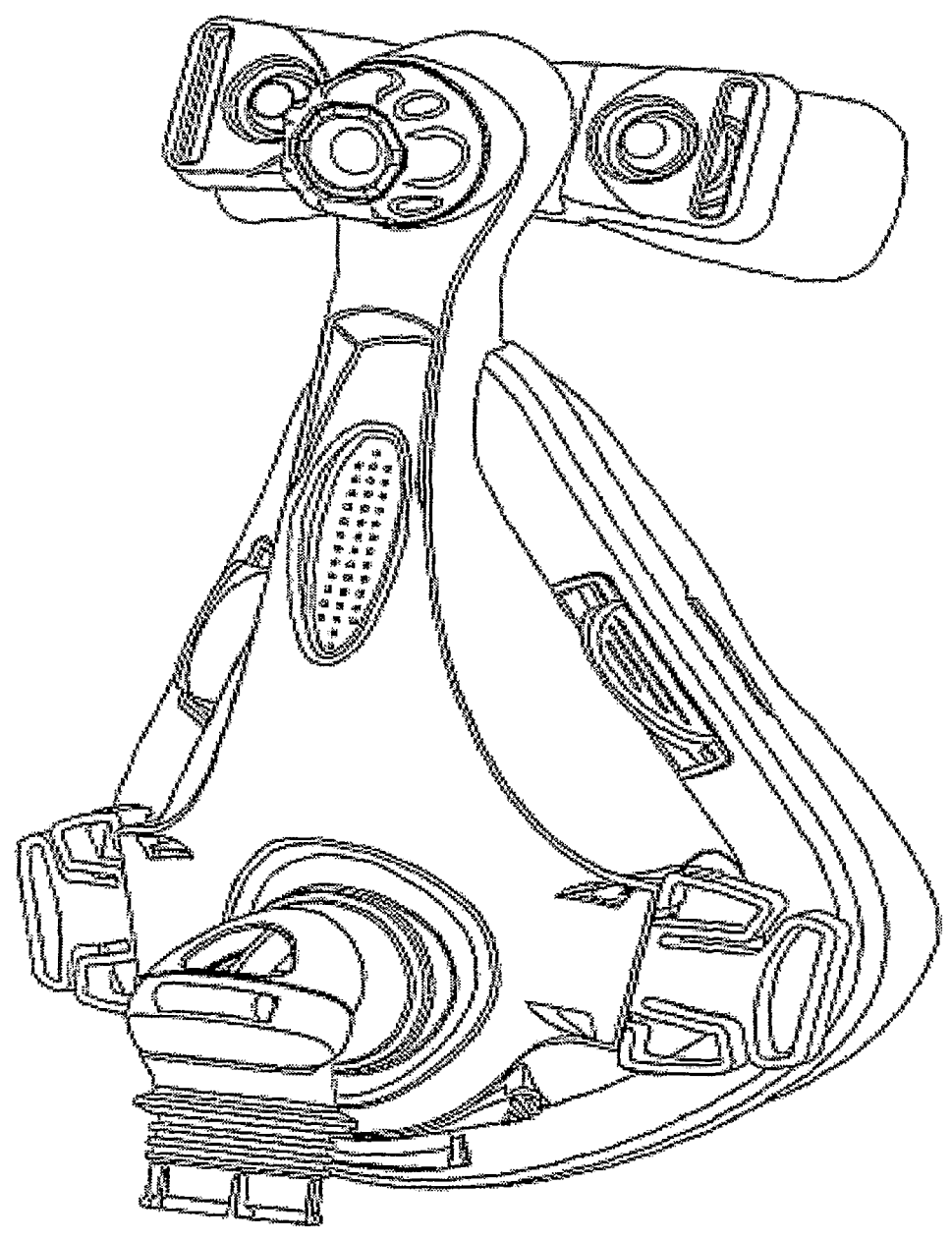
FIG. 17 depict a first example of a mask for use with the an example embodiment.
Figure 18:
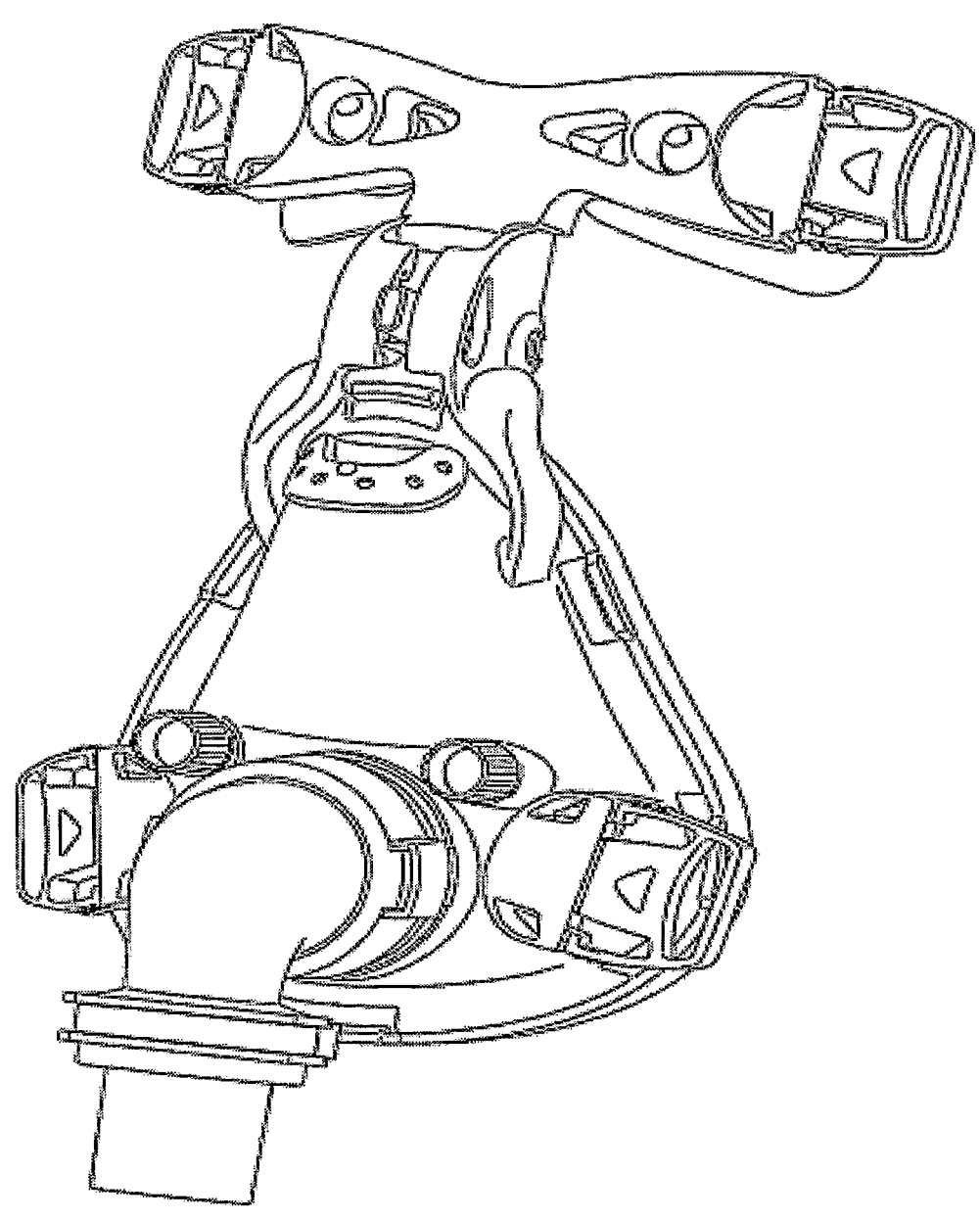
FIG. 18 depict a first example of a mask for use with the an example embodiment.

In the figure, the mask reflection can clearly be seen in all cases, beginning at around twelve milliseconds (12 ms). This time position is where it would be predicted since in the example system, a two meter tube was used and the speed of sound is 343 m/s. In FIG. 15, the graph depicts results from identifiable masks in the following order from top to bottom:

Ultra Mirage™ (shown in FIG. 18) using the flow generator FG at 10 krmp;

Ultra Mirage™, using the flow generator FG at 15 krmp;

Mirage Quattro™ (shown in FIG. 17) using the flow generator FG at 10 krmp;

Mirage Quattro™ using the flow generator FG at 15 krmp;

Swift II™ (shown in FIG. 16) using the flow generator FG at 10 krmp; and

Swift II™ using the flow generator FG at 15 krmp.

By increasing the overall tubing length, an appreciable increase in the delay of receiving the reflection from the mask may also be achieved. The increase in delay, when compared to FIG. 15, is in accordance with the aforementioned calculations generating the approximations of the tubing length.

In embodiments of the technology, data associated with the mask and/or tube reflection, such as that centrally illustrated in the graph of FIG. 15 may then be compared with similar data from previously identified mask (and/or tube) reflections such as that contained in a memory or Database of Mask Reflections.

For example, the "acoustic signature" of a tested mask may be separated, identified and filtered from the noisy measurement. This acoustic reflection data may be compared to that of previous or predetermined acoustic reflection data from known masks stored as a data template of the apparatus. One way of doing this is to calculate the cross correlation between the current measurement, and previously taken measurements for all known masks or data templates. There is a high probability that the cross correlation with the highest peak should correspond to correct mask, and the location of the peak on the time axis should be proportional to the length of the tube.

However, more points of correlation may also increase the accuracy of the detection and identification steps of the present embodiment. Thus, additional data points may be utilized. Optionally, a least squares algorithm with the test data and known data sets may be implemented in the mask/patient interface determination. Still further, in some embodiments additional feature extraction and recognition techniques may be utilized, which may be based on artificial intelligence strategies.

As with previous embodiments, the methodologies or signal processing described may be implemented by a controller or processor, such as with firmware, hardware and/or software as previously discussed. Such a controller may detect and/or identify the patient interface (which in this one embodiment is a mask, tubing or a combination thereof). This identification information or data relating to the presence or identity of the patient interface, may then be relayed to a further controller, processor, system or computer or used by the controller. The information then may be utilized in adjusting therapy or other settings for the control of the flow generator in the delivery of therapy by the respiratory treatment apparatus.

For example, the aforementioned technology may be implemented as part of a controller of a respiratory treatment apparatus such as a CPAP apparatus. Such an implementation may help to alleviate the need for users or clinicians of the CPAP apparatus to manually input or adjust the settings of the apparatus for use with particular patient interfaces or masks. Thus, some embodiments of the technology may even permit users to change masks without user input or setup being required for the CPAP apparatus since such a system may automatically set the apparatus with settings adjusted in accordance with the automatically identified patient interface or mask configuration.

Additionally, in some embodiments, the information relating to the identity or presence of the particular patient interface may be selectively sent or transmitted via the internet or some electronic means to a manufacturer, doctor or clinician so that the information may be used to assist user's or patient's with troubleshooting patient interfaces. For example, such data could be transmitted by wireless interfacing systems such as Bluetooth™ and/or Wi-Fi™.

Alternately, in some embodiments of the present technology, a controller may be utilized to detect whether the patient is currently wearing the patient interface based on the nature of the acoustic reflection, for example, by comparing test reflection data or cepstrum data to known reflection data or cepstrum taken during patient use. Similarly, the technology may be implemented to determine whether there is a technical problem with the patient interface including leaks and/or kinks in the system. This may also be detected by comparing current test reflection data or cepstrum data to a known reflection data or cepstrum data taken while the patient interface was in good working order and properly on a patient (e.g., no leak).

In some embodiments, greater speeds may be implemented during reflection testing/measuring from the speeds illustrated above. For example, some tubing or conduits use materials with properties that may reduce noise. In such a system, the acoustic losses of the system may actually fluctuate. If the losses increase as detected by the measured signal (e.g., amplitude decrease), the decibels of the sound or noise source may be increased to overcome the effects of sound loss. This may be achieved by increasing the speed of the flow generator during a test measurement. Additionally, other elements included in the air path of the mask or tubing may increase the acoustic losses. These elements may include: humidifiers, noise baffles, and valves. Again, the loss attributable to these components may also be overcome by increasing the noise source level or amplitude. Typically, a suitable noise or sound level from the sound source or flow generator may be about 20 dBa or greater.

As previously mentioned, some embodiments may utilize a sound source such as a speaker to generate a sound pulse or white noise. This may be particularly useful for respiratory treatment apparatus with very quiet flow generators that do not generate much noise. For example, when using a Resmed™ flow generator at speeds generally less than 6000 rpm, the flow generator is very quite. Under this condition, using the noise of the flow generator as an acoustic or noise emitter to produce the impulse might be insufficient. This may be overcome by including an additional noise emitter device either in the air conduit. This may be activated during time periods of measurement such as when the patient interface is initially attached to the flow generator. While a sound emitter might be a speaker, other emitters might be utilized. For example, a simple mechanical emitter might be implemented to vibrate in response to the flow of air from the flow generator such as a reed that may be selectively activated and deactivated (e.g., mechanically applied and removed from the flow path of the flow generator or conduit.) This may then serve to selectively create the sound impulse. Alternatively, an actuated valve of the respiratory treatment apparatus may serve as the sound source.

In some embodiments, the masks may be designed to have unique acoustic sound response characteristics. For example, a unique sound resonator may be designed within the mask or tubing to permit easier differentiation of the acoustic reflection signatures of each patient interface.

In some embodiments, autocorrelation (i.e., the inverse Fourier Transform of the power spectrum) may be implemented rather than using cepstrum analysis.

In further embodiments of the present technology, acoustic reflections may be analyzed to identify particular characteristics of patient interfaces in addition to identification of type or model. For example, system response data may be utilized to identify characteristics of patient masks and conduit tubing. The characteristics may include: diameter, construction materials, volume of air cavities, overall configurations of the masks and/or tubing, etc.

Furthermore, as discussed in more detail herein, some embodiments may also detect and measure the reflections or echoes returned from the patient's own respiratory system that is connected to the patient interface. For example, the embodied systems, methods, and devices may detect and identify the state, and conditioning of the patient's respiratory system or even an identity thereof for authentication purposes. For example, the apparatus may be implemented to detect the diameter of airways of a patient at any given point or points. Using the same or similar technique as previously discussed, closed airways or increased resistance in the patient's airways may be detected. Furthermore, the embodiments may also be able to detect whether the patient's mouth is open during CPAP treatment. Depending the problem or issue detected, the therapy may be adjusted accordingly. Such a system may also discern characteristics in the airpath between the flow generator FG and the patient's respiratory system (and including the patient interface located in between) (e.g., leaks or blockage). Furthermore, while masks and tubes have been discussed for use with the technology, some embodiments may also be implemented with nasal prongs. Nasal prongs may present minimal interruption to the airpath and may provide clearer acoustic reflection data concerning the patient's respiratory system.

For example, one or more leaks in the conduits of the respiratory treatment apparatus (e.g., disconnection) or even past the mask, such as a mouth leak, may be detected from the acoustic reflection data or cepstrum data. For example, because cepstrum data may be understood to provide information concerning the location of a noise reflection along a sound conduit as discussed in more detail herein, the present technology may permit an apparatus to discern the location of a leak in addition to whether a leak has occurred. For example, the leak may be identified and/or quantified by examination of cepstrum data such as comparing known stored cepstrum data representative of a leak to a current test cepstrum data. Once the leak is identified from the cepstrum data, the location (e.g., based on the timing of the leak related data in the cepstrum data) may be detected and a suitable response by the device may be made. For example, a detected mouth-to-mask contact leak (mouth leak) might have a different automated apparatus response from a leak detected in a conduit or tube near the flow generator. The apparatus might issue an audible warning for the latter while merely increasing the flow for the former.

Such a detector may be particularly suitable for high impedance tubing. For example, in 4 mm endotracheal ventilator tubing, the air passing through the tube generates a large amount of impedance. This impedance means that traditional methods of leak or accidental disconnection detection using pressure sensors or flow sensors struggle to identify the leak. Thus, the present technology may detect leaks or disconnection in low and high impedance tubing. Thus, such leak detection may also be suitable for implementation in high flow respiratory treatment devices that do not create pressurized therapy like CPAP devices. Such high flow devices typically utilize nasal prongs that do not seal against the inner walls of the nose. These high flow systems typically include high impedance conduits.

A. Patient/User Detection

Authentication or confirmation of a particular user of a particular device can have benefits. For example, limiting use of a medical device to a particular user may be significant for safety reasons. Consider a respiratory treatment device, such as a ventilator or continuous positive airway pressure device.

A patient using such a device may require particular settings for treatment, such as pressure delivery related settings. These settings may be prescribed by a physician. These settings may even be automatically determined or refined over periods of treatment of the patient with the device. Such settings may be only suitable for the particular patient and not others. It may be appropriate to configure such a device so that it may detect when a particular user or patient is using it or not so as to impede use by an unintended user.

It may be desirable for improved techniques and devices for authenticating a user of the device to confirm that use is for a particular person or impede use by others.

Accordingly, in the present technology automated devices provide methods of bio-acoustic user authentication. In some embodiments, a sound sensor determines a measure of sound of a sound generator within a sound conduit directed to an anatomical cavity of a user of a device. The measure of sound may be analyzed with a processor by calculation of a cepstrum from the measure of sound. The processor may then determine that the user is a pre-authorized user based on the analyzing. In certain example embodiments, the technology may be implemented as a safety feature for operation of a respiratory treatment apparatus so as to confirm likely use by a particular user.

Figure 19:
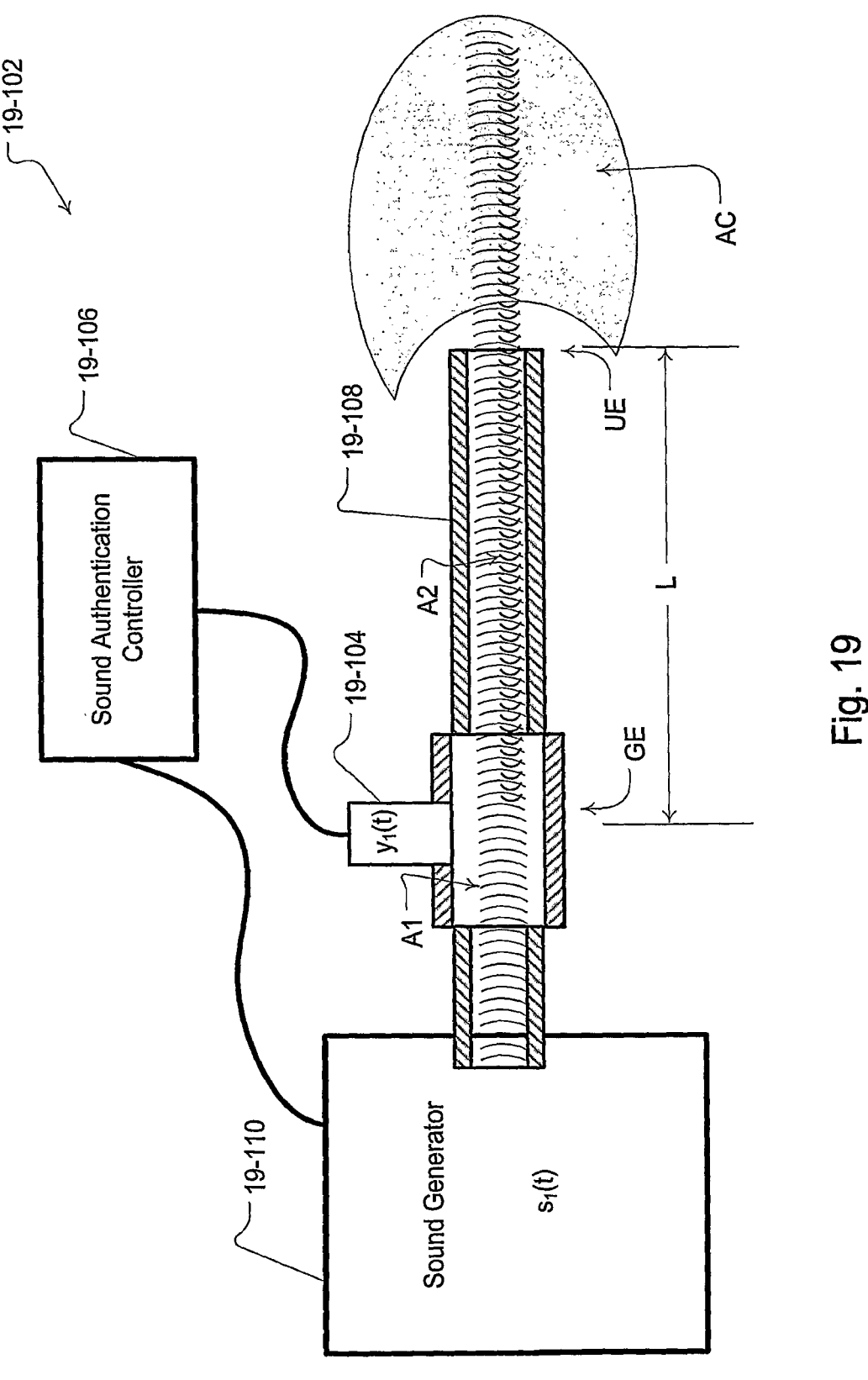
FIG. 19 illustrates example components of a system or apparatus for authenticating or detecting a particular user of a device of the present technology.

Thus, some embodiments of the present technology may involve methods and devices for user authentication or user detection. In a typical embodiment as illustrated in FIG. 19, the user detector apparatus 19-102 will include a sound sensor 19-104, such as a microphone, and a sound authentication controller 19-106. A sound conduit 19-108 in conjunction with a sound generator 19-110 can be configured to direct noise or sound to a user of a device with which the detector apparatus is combined. For example, the sound conduit 19-108 may be an endotracheal tube, CPAP mask, cannula, etc. in the case that the detector is combined with a respiratory treatment apparatus. Essentially, the conduit 19-108 assists in directing sound or noise waves (waves illustrated as A1 in FIG. 19) to an anatomical cavity AC of a user. In a typical embodiment, the sound sensor 19-104 measures sound traversing within a conduit 19-108 for analysis by the authentication controller 19-106. The sound may be that generated by a sound source. For example, the sound may be the vibrations or noise created by the operation of a flow generator such as a servo-controlled blower in the case of a respiratory treatment apparatus. For example, the flow generator may also be supplying a flow of breathable gas via the conduit 19-108 to the user's respiratory system. The measured sound can then include sound waves reflected from one or more anatomical cavities of a user of the apparatus.

Such a sound signal from the sound sensor 19-104 can be sent to the authentication controller 19-106. Optional analog-to-digital (A/D) converters/samplers (not shown separately) may be utilized in the event that supplied signal from the sensor is not in digital form and the controller is a digital controller. Based on the signal from the sensor, the controller assesses the sound signal to determine authentication data for comparison with previously determined authentication data.

In some embodiments, the authentication controller 106 may include a processor configured to implement particular detection methodologies such as the algorithms described in more detail herein. Thus, the controller may include integrated chips, a memory and/or other control instruction, data or information storage medium. For example, programmed instructions encompassing such a detection methodology may be coded on integrated chips in the memory of the device. Such instructions may also or alternatively be loaded as software or firmware using an appropriate data storage medium. With such a controller or processor, the device can be used for determining and analyzing sound data from the sound sensor. Thus, the processor may control the assessment for authentication or user detection as described in the embodiments discussed in more detail herein.

One example of such a methodology or algorithm of the controller 19-106 user detector apparatus 19-102 is illustrated in the flow chart of FIG. 20. At 20-220, a sound sensor measures sound of a sound generator within a sound conduit directed to an anatomical cavity of a user of a device. At 20-222, the measure of sound from the sound sensor is analyzed by the controller or a processor thereof by calculation of a cepstrum from the measure of sound. At 20-224, the controller or processor determines that the user is a pre-authorized user based on the analyzing. In such a case, the device may then permit operation or certain operations of the device. If it is determined that the user is not pre-authorized, certain operations or all operations of the device may be prevented by the authorization controller. Optionally, operations may be permitted or prevented by sending an enable or disable signal(s) from the authorization controller 19-106 to another controller of the device.

In such embodiments of the technology, there may be a number of design considerations relating to the acoustic nature of the system and the desire to isolate acoustic information associated with the user's anatomical cavity for identification purposes. The components used to direct sound thereto can have many different configurations that may yield different acoustic properties. One example conduit component may be a tube having an approximately constant cross section along its length "L", with the user's anatomical cavity at a user end of the conduit (shown as "UE" in FIG. 19), and the sound generator (with other potential components) at the sound generator end (shown as "GE" in FIG. 19). An acoustic characteristic of the conduit may be that it acts as a wave guide for a wide range of frequencies along its length.

Thus, in some embodiments of the apparatus, detecting a user by the acoustic properties of the anatomical cavity might be based on the acoustic reflection in a conduit during sound generator operations by comparing data measured during a setup procedure while being worn by a user and test data measured as a before a user attempts to begin or continue some operations of the device.

The Impulse Response Function ("IRF") of the sound or noise in such a system created by a sound generator as a sound source to a sound sensor can contain a delta function at a chosen time zero, and a reflection from the anatomical cavity at time greater than 2L/c, where the speed of sound is denoted by "c", and the length of the conduit is "L". Such data of the reflection may be recorded and stored during a set-up process for subsequent analysis. Thereafter, if the user wishes to use the device, another IRF of the system may record a new reflection at time greater than 2L/c from the anatomical cavity for comparison with the original set-up data. A significant change in the reflection may be indicative of a different user whereas an unsubstantial difference or identity in the reflection data may be indicative of the same user from the set-up process.

As previously discussed, one potential method for monitoring for such a change or similarity in the reflection from the conduit may be based on the calculation of a cepstrum of a signal from the sound sensor.

By comparing cepstrum data from the conduit and anatomical cavity of a pre-authorized user with cepstrum data from the conduit and anatomical cavity of a subsequent user, the comparison, such as differences there between, may be considered in identifying the user. For example, if a common noise source is used in both tests, the comparison or difference between the cepstrum data of both tests may be considered an indication that the present user is not the same as the user of the set-up process or that the present user is the same as the user of the set-up process.

Some factors of the IRF (from the sound generator as a sound source to the microphone response) are herein explained. When the conduit acts as a wave guide for sound produced by the sound generator, sound is emitted and forms a first signal (illustrated in FIG. 19 as "A1"). The sound or first signal travels down or along the conduit, which may or may not have a significant length, to the anatomical cavity and is reflected back along the conduit. The reflected sound may be considered a second signal (illustrated in FIG. 19 as "A2"). As previously mentioned, a feature of the example conduit response is the time required by sound to travel from one end of the system to the opposed end. This delay may mean that the sound sensor positioned at one end of the conduit receives the first signal coming from the sound generator, and then some time later receives the same sound filtered by the conduit as reflected second signal A2 (and potentially any other system attached, like human respiratory system). This may mean that the part of the IRF associated with the reflection from the anatomical cavity appears after a delay. The delay may be considered approximately equal to the time taken for sound to travel from the sound source to the anatomical cavity, be reflected, and travel back again.

When the system is loss-prone, given the length of the conduit, the part of the IRF associated with the response at the sound generator will decay to a negligible amount by the time the reflection response has begun. When this occurs, the response due to the anatomical cavity may be completely separated from the sound generator response in the system IRF.

In the case that a sound source is a noise generator, the methodology and system for separating the anatomical cavity reflection from the convolutive mixture may be that as explained in previous embodiments.

Thus, in some embodiments, a continuous sound of sound generator may be taken as the sound impulse to the system by considering an arbitrary point in time during the continuous sound to be the sound impulse. In such a case, the sound generator would not need to produce periods of silence or reduced sound before and after a relative increase in sound to thereby produce an actual momentary sound impulse. However, in some embodiments such a momentary sound impulse may be generated by modulation of the sound control signals to the sound generator or sound source. For example, in the case of the flow generator serving as a sound source a constant motor speed may be implemented to generate the noise. Alternatively, modulation may be implemented by setting low or no speed, followed by an instantaneous high speed and then followed by a return to the low or no speed. Other methods of implementing a momentary sound impulse may also be implemented such as a speaker implementing chirp or other acoustic sound.

Figure 21:
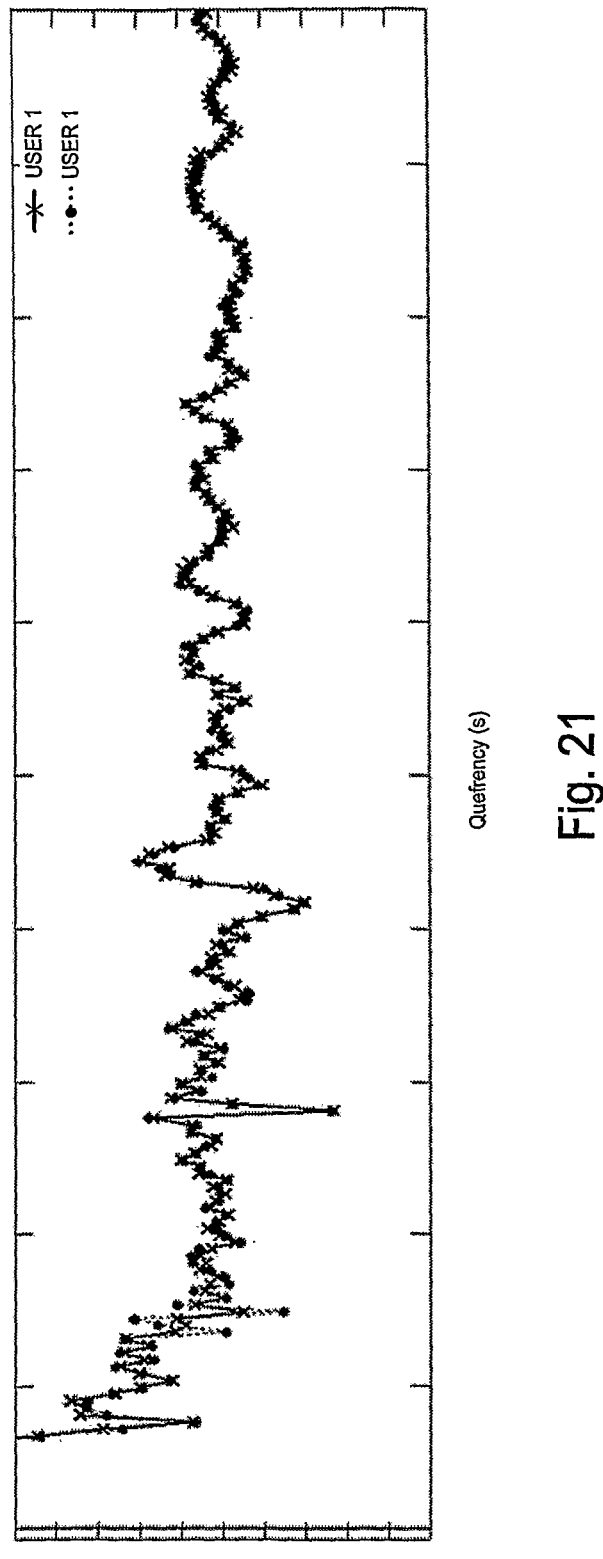
FIG. 21 is a graph of hypothetical cepstrum data from two sound waves measured from a common user at different times.

FIGS. 21 through 24 show hypothetical data graphs illustrating an analysis of sound data from a microphone to detect a user by sound reflection associated with an anatomical cavity based on the previously described cepstrum methodology. In FIG. 21, data from two distinct sound measurement tests (e.g., a set-up process and subsequent user authentication process) are plotted on a common axis. Sound can be measured such that samples of the microphone signal may be collected or recorded from a chosen or controlled time zero until a sufficient period of time has lapsed to permit the sound to traverse the conduit beyond the user end, reflect from the anatomical cavity and return to the microphone. In both cases illustrated in FIG. 21, the anatomical cavity subjected to the measurement process was confirmed to be that of the same user. The measurement samples or sound data from the microphone in each test would be subjected to the operations described by equations 1, 2, 3 and 4 previously mentioned. The result of this process is illustrated in the graphs.

Figure 22:
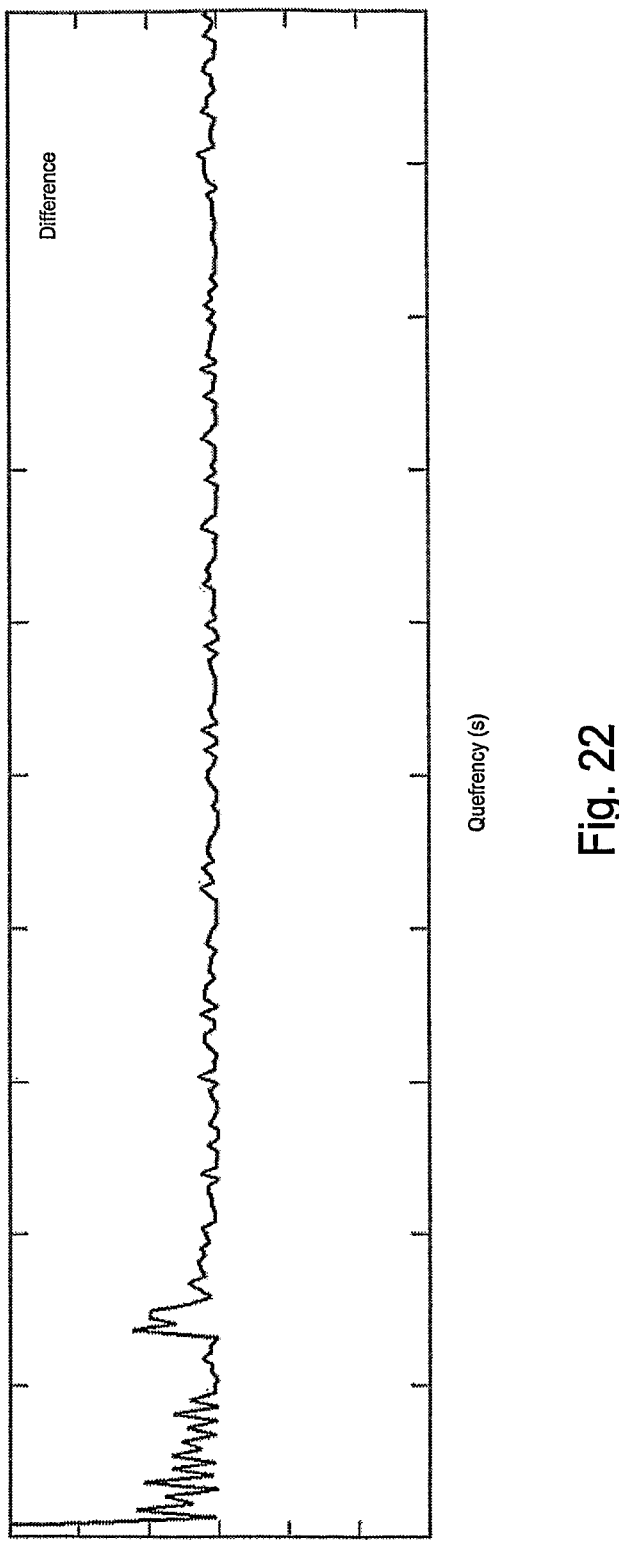
FIG. 22 is a graph of the difference of the cepstrum data from the two sound waves of FIG. 21.

In FIG. 22, the difference or magnitude of the difference from the data of the two plots of FIG. 21 is shown. Such a difference or magnitude may optionally be determined on a sample-by-sample basis as the absolute value of the difference between the sound data of the two tests. The approximately flat line having no significant samples may be taken as a representation that the device has properly detected the user (or her anatomical cavity) who had been tested and associated with the device in a set-up process. In an example process, the samples of the difference data may be evaluated by a threshold value to assess their significance.

Figure 23:
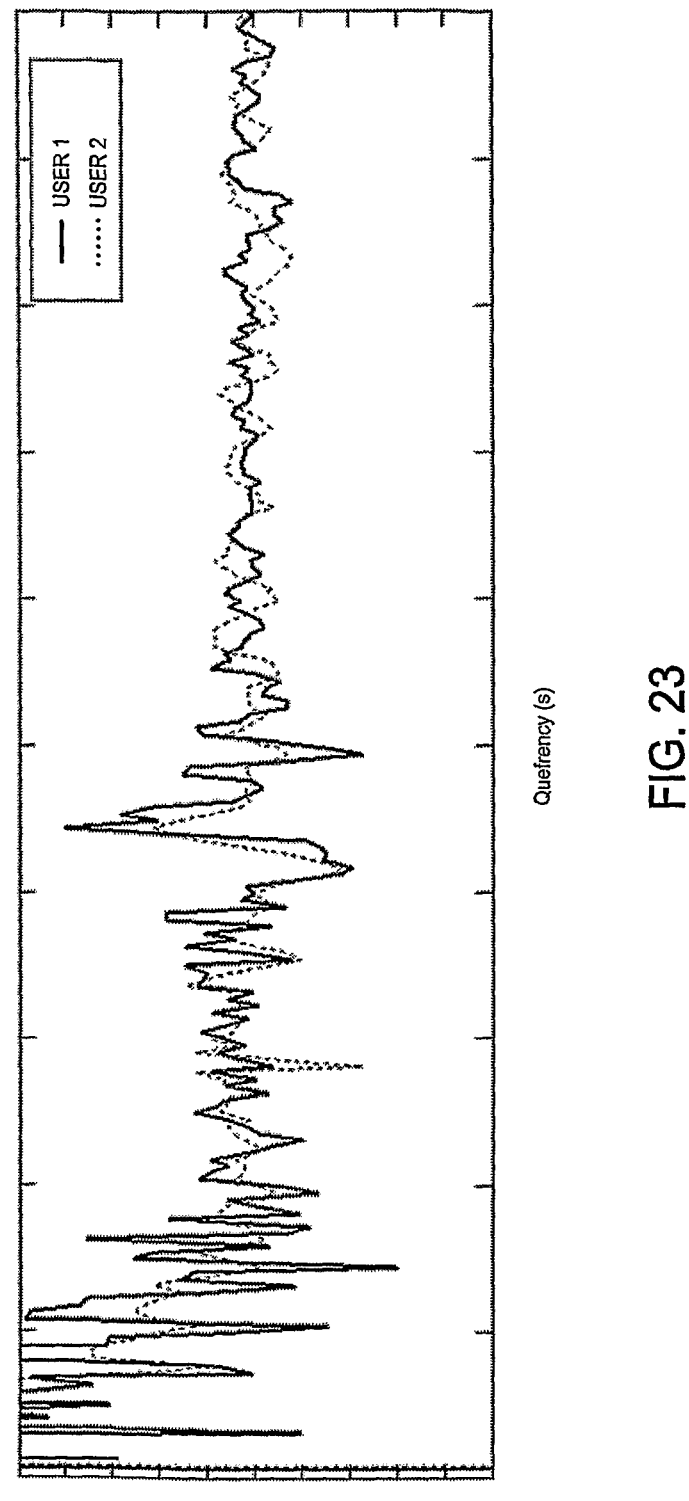
FIG. 23 is a graph of hypothetical cepstrum data from two sound waves taken from two different users.
Figure 24:
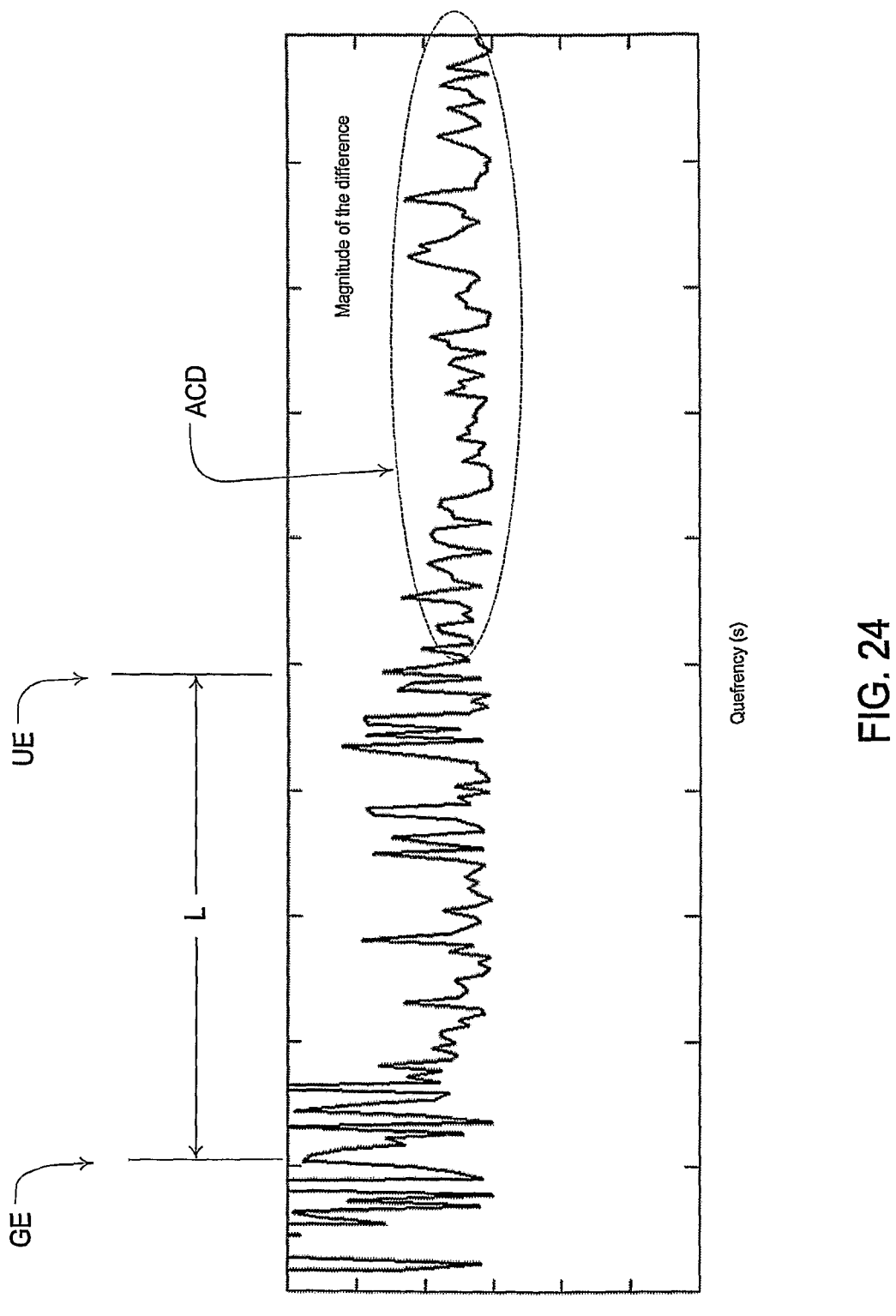
FIG. 24 is a graph of a magnitude of the difference in the cepstrum data from the two sound waves of FIG. 23.

In FIG. 22, hypothetical data from two distinct sound measurement tests are again plotted on a common axis. In one case the conduit subject to the measurement process was coupled with an anatomical cavity of a first user (USER 1) and in the other case the conduit of the measurement process was coupled with an anatomical cavity of a second, different user (USER 2). The sound data from the microphone in each test can be subjected to the operations described by equations 1, 2, 3 and 4 previously mentioned and then plotted. In FIG. 23, the difference or magnitude of the difference from the data of the two plots can then be determined on a sample-by-sample basis and plotted. The presence of any significant difference in one or more samples (e.g., one or more values in excess of a threshold at a point along the plot) may be representative of an unauthorized user or user who did not participated in the measurements of the set-up process. Such a determination may be made by scanning and assessing the samples of the difference data. Optionally, data samples with information beyond the end of the conduit particularly associated with the acoustic reflection of the anatomical cavity may be the focus of the analysis. Such samples or data are illustrated in FIG. 24 with the reference character ACD. In this regard, given the known length of the conduit, the data of the plot beyond the conduit end may be assessed given that the cepstrum data is a function of seconds as follows:

$$Ts>=(2\times L)/C$$

Where:
Ts is a time position of a sample in seconds; and
L is the known length of the conduit; and
C is the speed of sound.
It will be understood that this calculation may be adjusted to account for the distance from the microphone to the sound generator end of the conduit.

Based on the comparison between the cepstrum data determined in an authentication test process and the cepstrum data previously determined during a set-up process, a device may be controlled so as to limit or permit operations upon confirmation that examined cepstrum data is sufficiently similar or not sufficiently similar. For example, based on the cepstrum analysis, a detection of a significant value or values in the cepstrum difference data may be taken as being indicative of a different anatomical cavity or a different user. In such a case, the authentication controller may be implemented to disable (or enable) one or more operations of the device that includes the user detector apparatus 19-102 depending on the desired consequence of the authentication results.

While this technology might be implemented as a method to uniquely authenticate a single person of a protected device, it is recognized that such a unique authentication of a particular user may not be strictly necessary. Thus, benefits described herein may still be achieved if the implemented authentication system precludes some or most other possible users while still allowing the originally verified user to use the protected device.

As previously mentioned, the user detector apparatus 19-102 may be configured with a pre-measuring set-up process to establish a basis for cepstrum data of an anatomical cavity of a verified, known or authorized user. For example, when the device is first operated the set-up process may be triggered. Alternatively, data from such a process may be pre-stored into the user detector apparatus from another device. When subsequent authentication tests are made by the apparatus, such as in an automatic start-up process, the subsequent test measurement data may be used for comparison with the pre-stored data to confirm use by the authorized or intended user.

Optionally, in addition to or as an alternative to disabling the device, the detector may trigger a warning message and/or alarm to identify that the device is intended for a different user. Thus, a controller of such an apparatus may optionally include a display device such as one or more warning lights (e.g., one or more light emitting diodes). The display device may also be implemented as a display screen such as an LCD. Similarly, detection of a different or unintended user may trigger a new initialization of the particular device protected by the user detection apparatus so that the operations of the device will commence with settings suitable for all users rather than the settings that may have been particularly determined for a particular user.

Figure 25:
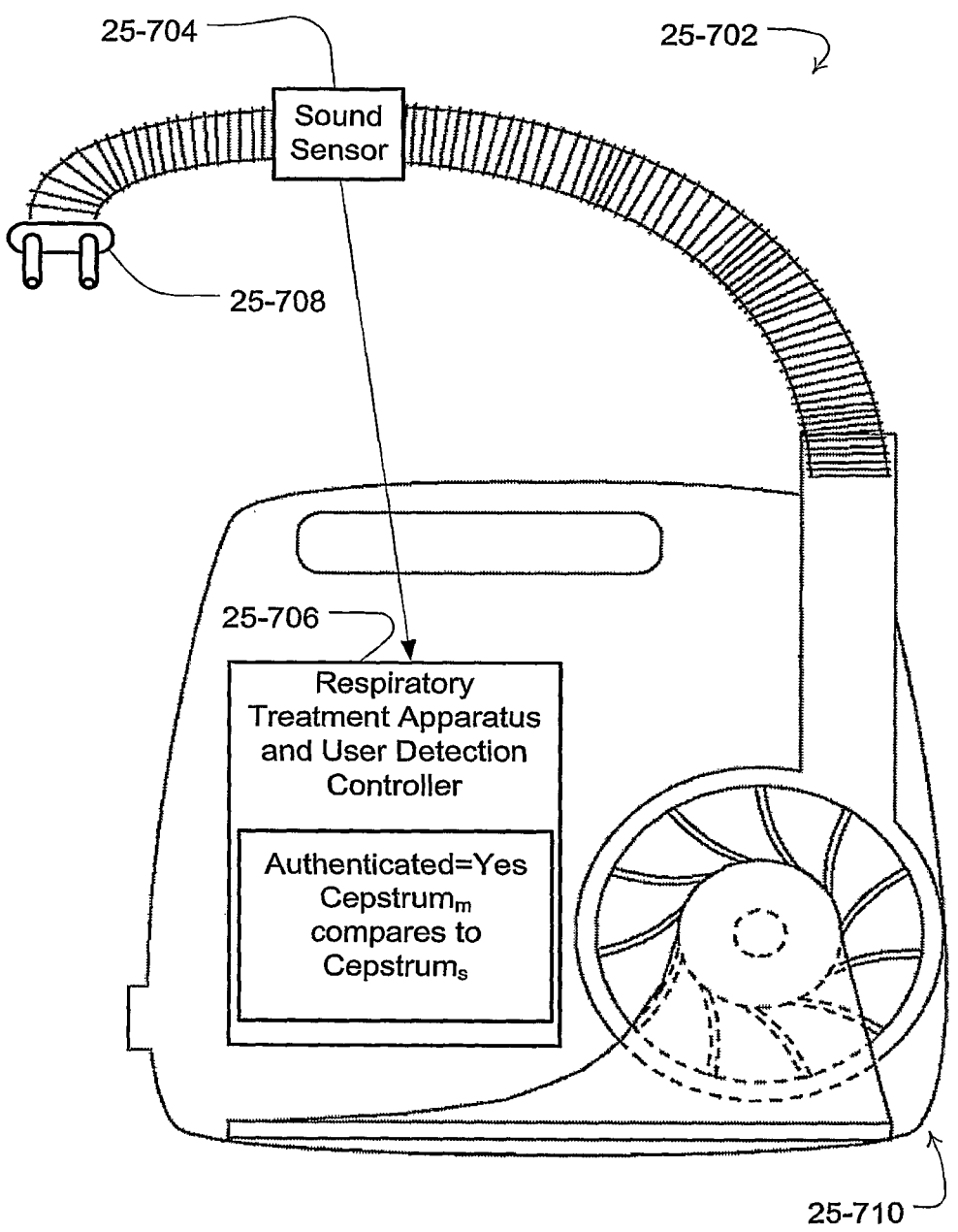
FIG. 25 is an illustration of components of an example respiratory treatment apparatus configured with authentication technology in accordance with some embodiments of the present technology.

As previously mentioned and illustrated in FIG. 25, an example detector 25-702 of the present technology may be implemented as a respiratory treatment apparatus. In such an embodiment, the sound sensor may be integrated with a respiratory treatment apparatus conduit (e.g., an endotracheal tube or ventilator supply conduit) or installed in a part of a conduit coupler, mask or nasal cannula. In the example of FIG. 25, a microphone may be installed in a conduit that also serves to direct a supply of air to a patient's respiratory system such as the nares and/or mouth of a patient. In such a case, one or both nares and/or the mouth may serve as the anatomical cavity or cavities for user detection.

In further reference to the example embodiment of FIG. 25, a controller 25-706 that controls the delivery of pressure or ventilation treatment of a patient via a flow generator, may also serve as the user authentication or user detection controller. In such an embodiment, the sound sensor 25-704 may be directly coupled with the controller 25-706 of the respiratory treatment apparatus for the acoustic measurements in the conduit 25-708. Such a device may also include a pressure sensor, such as a pressure transducer to measure the pressure generated by the blower 25-710 and generate a pressure signal p(t) indicative of the measurements of pressure. It may also optionally include a flow sensor. Based on flow f(t) and pressure p(t) signals, the controller 25-706 with a processor may generate blower control signals if such operations are permitted or enabled by the methodology of the user detection controller as previously discussed.

Thus, the controller may generate a desired pressure set point and servo-control the blower to meet the set point by comparing the set point with the measured condition of the pressure sensor. Thus, the controller 25-706 may make controlled changes to the pressure delivered to the patient interface by the blower 25-710. Optionally, it may include a speed sensor so as to control the blower to a particular RPM setting. In this regard, in addition to automated respiratory treatment, the blower may serve as a source of noise or sound generator during the acoustic measuring as previously described such as by running the blower at a constant speed during the time period of the sound sensor's measurement.

Figure 26:
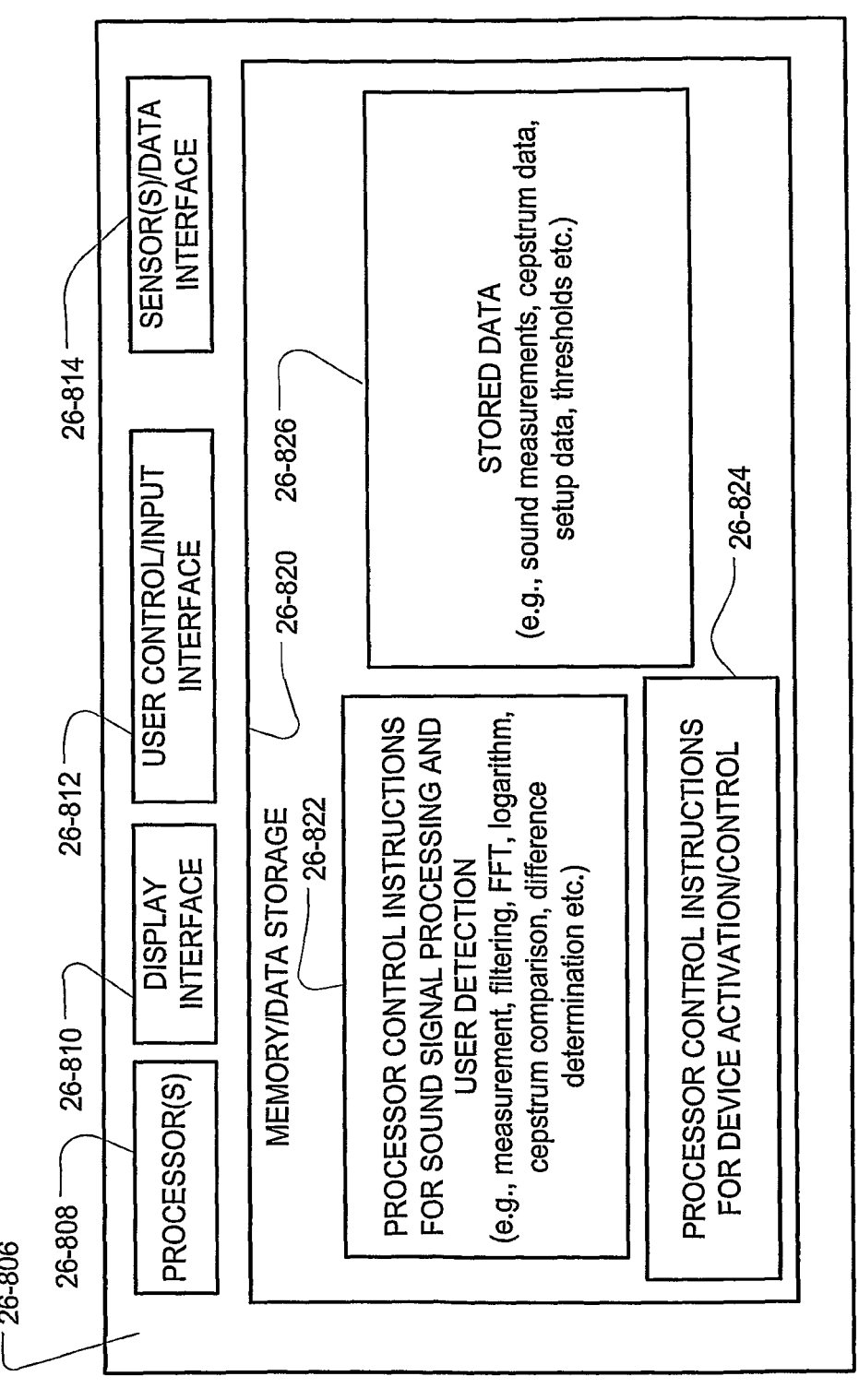
FIG. 26 illustrates a block diagram of an example controller architecture of the present technology with user detection technology.

An example architecture for a user detection controller 26-806 is illustrated in the block diagram of FIG. 26. In the illustration, the controller may be implemented by one or more programmable processors 26-808. The controller may also include a display interface 26-810 to output data for a user interface or display device as previously discussed (e.g., warnings or messages, etc.) such as on a monitor, LCD panel, touch screen, etc. A user control/input interface 26-812, for example, for a keyboard, touch panel, control buttons, mouse etc. may also optionally be included for inputting data, or otherwise activating or operating the methodologies described herein. The device may also include a sensor or data interface 26-814, such as a bus, for receiving/transmitting data such as programming instructions, settings data, sound data, microphone sound samples, acoustic measurement data, cepstrum data, etc.

The controller also includes memory/data storage components 26-820 containing control instructions and data of the aforementioned methodologies. For example, at 26-822, they may include stored processor control instructions for sound signal processing and user authentication/detection processing, such as, measurement, filtering, FFT, logarithm, cepstrum comparison/assessment, difference determination etc. At 26-824, these may also include stored processor control instructions for device activation or control, such as such as the instructions for which operations are permitted or prevented in accordance with the user detection/authentication. Finally, they may also include stored data at 26-826 for the methodologies such as sound measurements, cepstrum data, set-up data, thresholds etc.

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software and data into the general purpose computer.

While the authentication or user detection technology has been described in several embodiments, it is to be understood that these embodiments are merely illustrative of the technology. Further modifications may be devised within the spirit and scope of this description.

For example, while an integrated user authentication control device is contemplated by the present technology, the methodology of the components of the device may be shared across multiple components of a system. For example, a measuring device may simply conduct the measuring processes to determine the acoustic data of the conduits and transfer the data to another processing system. The second processing system may in turn analyze the data to determine the authentication as previously discussed. The second processing system may then indicate the authentication as described herein, such as by sending one or more of the described enabling or disabling messages, in electronic form for example, back to the measuring apparatus or other device, for control of the operations of a device.

Similarly, while the technology contemplates embodiments where data from only a single microphone may be implemented to detect the user, in some embodiments of the technology additional microphones may be implemented. Moreover, while the technology contemplates embodiments where the noise or sound of the system that serves as the sound impulse is the sound generated by a flow generator operating at one or more chosen blower settings, in some embodiments, a speaker or horn driver may be implemented in the conduit to generate the sound impulse that is recorded by the sound sensor.

In some embodiments, the technology may also be implemented with a sound generator that is an audio device such as a digital audio file player, such as a hand-held device. The components of the audio device may include a user detector as previously described and may be configured to generate sound into auditory canal(s) using the conduit of an ear plug or ear speakers for authentication. Operation(s) of the audio device may then be enabled or disabled based on a microphone of the ear plug or ear speakers and a processor of the audio device configured with the sound detection methodologies as previously described.

B. Further Embodiments

Other variations can be made without departing with the spirit and scope of the technology. For example, any of the described features of the aforementioned embodiments (e.g., obstruction detection features, component detection features and user detection features) may be combined together to form various additional apparatus so as to include the benefits of the various functionalities disclosed.

In some embodiments, the acoustic detection methodologies may be implemented without an automated sound source such as a sound speaker or an operating flow generator. For example, a user of a mask may create a sound pulse by making a sound (e.g., humming) into the mask which may then be measured by the apparatus for some of the detection methodologies previously mentioned. This sound reflection might then be used to identify the mask by the processing of the controller of apparatus.

The invention claimed is:

1. A respiratory therapy apparatus configured to generate a supply of pressurized air from an outlet and along an artificial airpath to a patient interface for a respiratory therapy, the respiratory therapy apparatus comprising:
   a motor and impeller adapted to generate the supply of pressurized air;
   a sensor configured to receive and transduce (a) a first acoustic signal generated by operation of the motor and impeller, and (b) a second acoustic signal (i) representative of the first acoustic signal having been reflected back from the patient interface along the artificial airpath, and (ii) corresponding to the patient interface; and
   a controller comprising one or more processors and coupled with the sensor, the controller configured to:

generate one more signals for operating the motor and impeller to generate the supply of pressurized air, as the respiratory therapy, to the patient interface;

process the transduced first acoustic signal and second acoustic signal; and detect the patient interface that is connected to the artificial airpath based on the processed transduced second acoustic signal, wherein the controller is configured to identify, using the processed transduced second acoustic signal, a model of the patient interface so as to differentiate the model of the patient interface from other patient interface models.

2. The respiratory therapy apparatus of claim 1, wherein the first acoustic signal is either an acoustic impulse or a continuous acoustic signal.

3. The respiratory therapy apparatus of claim 1, wherein the controller processes the transduced first and second acoustic signals by cepstrum analysis.

4. The respiratory therapy apparatus of claim 1, wherein the sensor is one of the group consisting of: a microphone; a pressure sensor; and a flow sensor.

5. The respiratory therapy apparatus of claim 1, wherein the controller is further configured to transfer information about the connected patient interface to a computer.

6. The respiratory therapy apparatus of claim 1, wherein the sensor is mounted or encapsulated in or positioned proximal to the outlet of the respiratory therapy apparatus.

7. The respiratory therapy apparatus of claim 1, wherein the detecting further comprises (a) identifying a mask model, or (b) detecting a leak associated with the patient interface.

8. The respiratory therapy apparatus of claim 1, wherein to process and detect, the controller is configured to evaluate quefrency data.

9. The respiratory therapy apparatus of claim 8, wherein to process and detect, the controller is configured to compare measured and stored responses represented by the quefrency data.

10. The respiratory therapy apparatus of claim 9, wherein to compare the measured and stored responses, the controller is configured to compute a cross-correlation of the measured and stored responses, and detect one or more peaks in the cross-correlation.

11. The respiratory therapy apparatus of claim 10, wherein the controller is configured to evaluate a time position of the detected one or more peaks.

12. The respiratory therapy apparatus of claim 9, wherein to compare the measured and stored responses, the controller is configured to perform a least squares operation with the measured and stored responses.

13. The respiratory therapy apparatus of claim 1, wherein the controller is further configured to adjust a setting of the respiratory therapy apparatus based on the identified model of the patient interface.

14. The respiratory therapy apparatus of claim 13, wherein in response to the detection, the controller selects (a) operating parameters of the respiratory therapy apparatus or (b) settings for control of the respiratory therapy apparatus.

15. The respiratory therapy apparatus of claim 1, wherein the controller is configured to operate the motor and impeller to produce the first acoustic signal.

16. The respiratory apparatus of claim 1, wherein the respiratory therapy comprises a positive pressure therapy.

17. A method for operating a respiratory therapy apparatus comprising a motor and impeller configured to generate a supply of pressurized air from an outlet and along an artificial airpath to a patient interface for a respiratory therapy, the method comprising:

operating a sensor to transduce (a) a first acoustic signal generated by operation of the motor and impeller, and (b) a second acoustic signal (i) representative of the first acoustic signal having been reflected back from the patient interface along the artificial airpath, and (ii) corresponding to the patient interface; and with a controller coupled with the sensor:

processing the transduced first acoustic signal and the second acoustic signal, and detecting the patient interface connected to the artificial airpath based on the processed second acoustic signal, wherein the controller identifies, using the processed transduced second acoustic signal, a model of the patient interface so as to differentiate the model of the patient interface from other patient interface models; and controlling an operation of the motor and impeller to generate the supply of pressurized air, as the respiratory therapy, to the patient interface.

18. The method of claim 17, wherein the processing the transduced first and second acoustic signals comprises performing a cepstrum analysis.

19. The method of claim 17, wherein the sensor is one of the group consisting of: a microphone; a pressure sensor; and a flow sensor.

20. The method of claim 17, further comprising, with the controller, (a) transferring information about the connected patient interface to a computer; and/or (b) operating the motor and impeller to produce the first acoustic signal.

21. The method of claim 17, wherein the sensor is mounted or encapsulated in or positioned proximal to the outlet of the respiratory therapy apparatus.

22. The method of claim 17, wherein the detecting further comprises (a) identifying a mask model, or (b) detecting a leak associated with the patient interface.

23. The method of claim 17, the processing comprises evaluating quefrency data.

24. The method of claim 23, wherein the processing comprises comparing measured and stored responses represented by the quefrency data.

25. The method of claim 24, wherein the comparing the measured and stored responses, comprises computing a cross-correlation of the measured and stored responses, and detecting one or more peaks in the cross-correlation.

26. The method of claim 25, further comprising evaluating a time position of the detected one or more peaks.

27. The method of claim 24, wherein the comparing the measured and stored responses comprises performing a least squares operation with the measured and stored responses.

28. The method of claim 17, further comprising, by the controller, adjusting a setting of the respiratory therapy apparatus based on the identified model of the patient interface.

29. The method of claim 28, wherein in response to the detection, the controller selects (a) operating parameters of the respiratory therapy apparatus, or (b) settings for control of the respiratory therapy apparatus.

30. The method of claim 17, wherein the respiratory therapy comprises a positive pressure therapy.

* * * * *